(12) United States Patent
Terliuc et al.

(10) Patent No.: US 11,247,029 B2
(45) Date of Patent: Feb. 15, 2022

(54) BALLOON-EQUIPPED ENDOSCOPIC DEVICES AND METHODS THEREOF

(71) Applicant: SMART Medical Systems Ltd., Ra'anana (IL)

(72) Inventors: Gad Terliuc, Ra'anana (IL); Gilad Luria, Givataim (IL)

(73) Assignee: SMART Medical Systems Ltd., Ra'anana (IL)

( * ) Notice: Subject to any disclaimer, the term of this patent is extended or adjusted under 35 U.S.C. 154(b) by 0 days.

(21) Appl. No.: 16/665,268

(22) Filed: Oct. 28, 2019

(65) Prior Publication Data
US 2020/0164186 A1 May 28, 2020

Related U.S. Application Data

(63) Continuation of application No. 14/003,799, filed as application No. PCT/IL2012/000003 on Jan. 5, 2012, now Pat. No. 10,456,564.

(60) Provisional application No. 61/457,351, filed on Mar. 7, 2011.

(51) Int. Cl.
| | | |
|---|---|---|
| *A61B 1/015* | (2006.01) | |
| *A61B 1/018* | (2006.01) | |
| *A61B 1/273* | (2006.01) | |
| *A61B 1/31* | (2006.01) | |
| *A61M 25/10* | (2013.01) | |
| *A61B 1/00* | (2006.01) | |
| *A61M 25/04* | (2006.01) | |

(52) U.S. Cl.
CPC ... *A61M 25/10181* (2013.11); *A61B 1/00039* (2013.01); *A61B 1/015* (2013.01); *A61B 1/018* (2013.01); *A61B 1/2733* (2013.01); *A61M 25/10185* (2013.11); *A61B 1/00082* (2013.01); *A61B 1/31* (2013.01); *A61M 25/04* (2013.01); *A61M 25/10184* (2013.11); *A61M 2025/1086* (2013.01)

(58) Field of Classification Search
CPC ... A61B 1/00082; A61B 1/00101; A61B 1/01; A61B 1/31
USPC .................. 600/101, 104, 114–115; 606/1, 9
See application file for complete search history.

(56) References Cited

U.S. PATENT DOCUMENTS

| | | | | |
|---|---|---|---|---|
| 8,348,889 B2 * | 1/2013 | Salemi | ................... | A61M 25/04 604/101.01 |
| 9,808,142 B2 * | 11/2017 | Axon | ................. | A61B 1/00075 |
| 2004/0077926 A1 * | 4/2004 | Moriyama | ......... | A61B 1/00089 600/101 |
| 2004/0210116 A1 * | 10/2004 | Nakao | ................ | A61B 1/00082 600/204 |

(Continued)

FOREIGN PATENT DOCUMENTS

| | | |
|---|---|---|
| JP | H120286223 | 10/1998 |
| JP | 2000189385 | 7/2000 |
| JP | 2005205181 | 8/2005 |

*Primary Examiner* — Matthew J Kasztejna
(74) *Attorney, Agent, or Firm* — Knobbe, Martens, Olson & Bear, LLP

(57) ABSTRACT

An endoscopy system including a balloon-equipped endoscope including a balloon which is configured for slidable frictional engagement with an interior wall of a body passageway and axial stretching of the interior wall when inflated to a slidable frictional engagement pressure and displaced axially along the body passageway and a balloon inflation subsystem operative to selectably inflate the balloon to the slidable frictional engagement pressure.

18 Claims, 14 Drawing Sheets

(56) References Cited

U.S. PATENT DOCUMENTS

| | | | | |
|---|---|---|---|---|
| 2005/0159645 A1* | 7/2005 | Bertolero | ............... | A61B 5/064 |
| | | | | 600/116 |
| 2008/0177142 A1* | 7/2008 | Roskopf | ............ | A61B 1/00082 |
| | | | | 600/115 |
| 2009/0012469 A1* | 1/2009 | Nita | ................. | A61B 17/22012 |
| | | | | 604/104 |

* cited by examiner

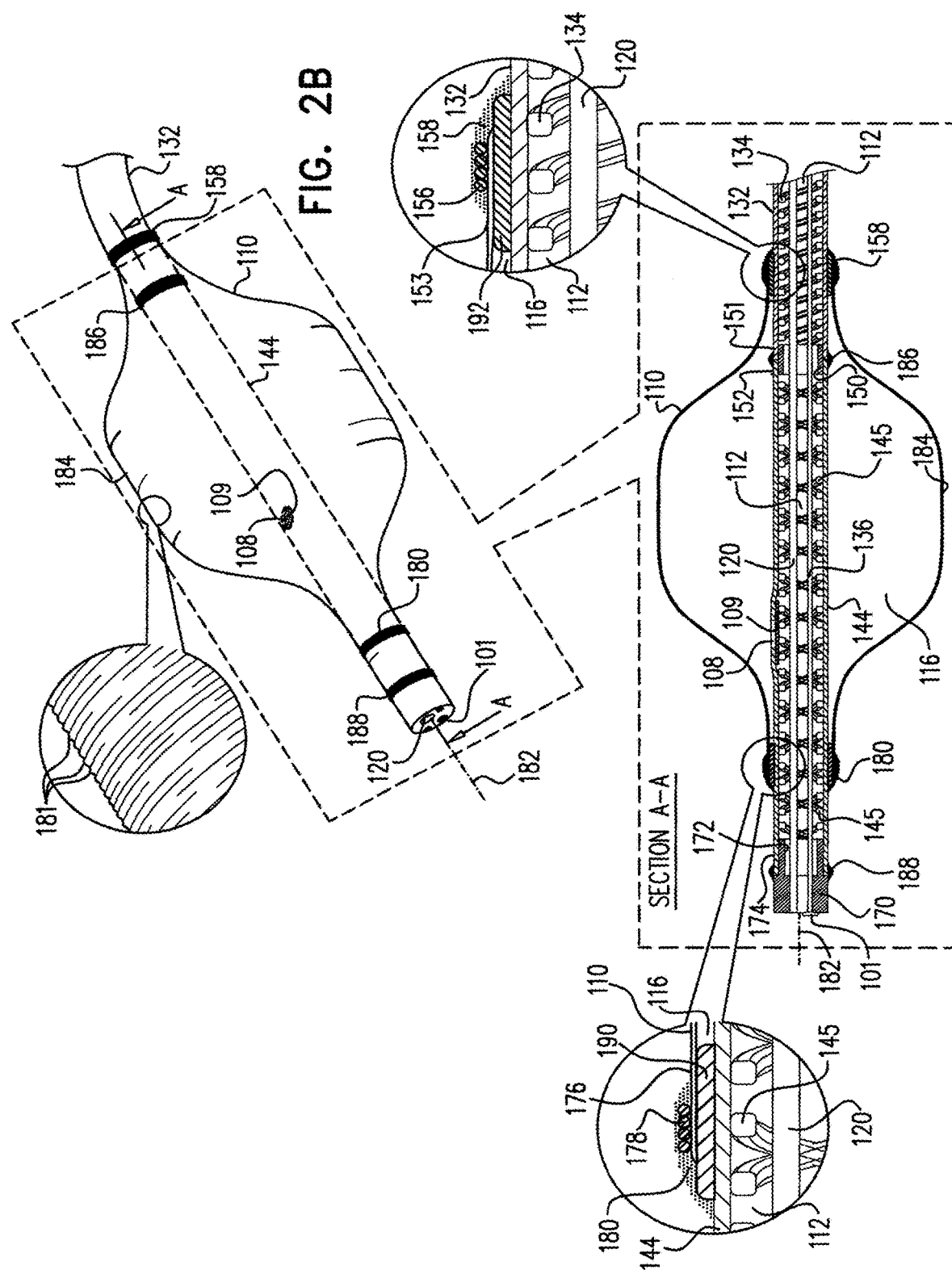

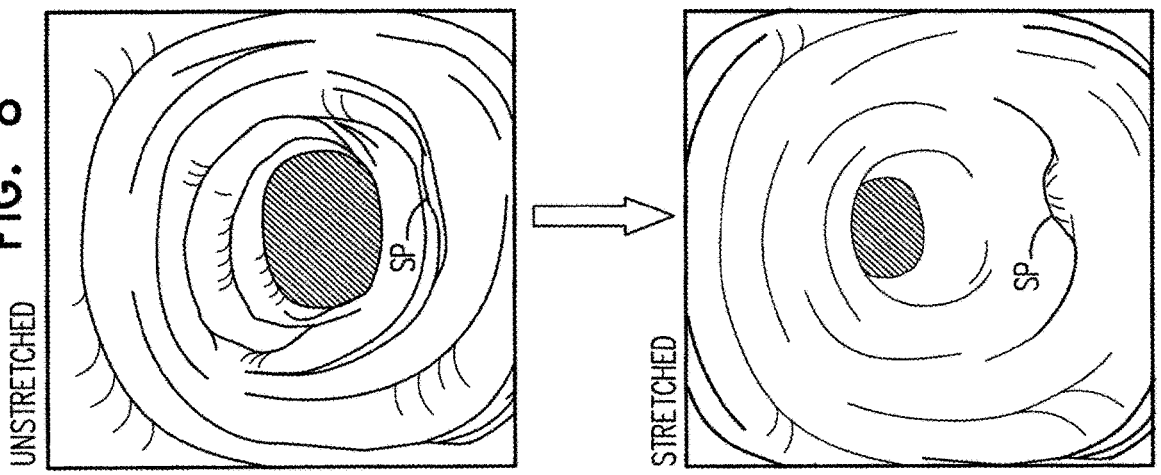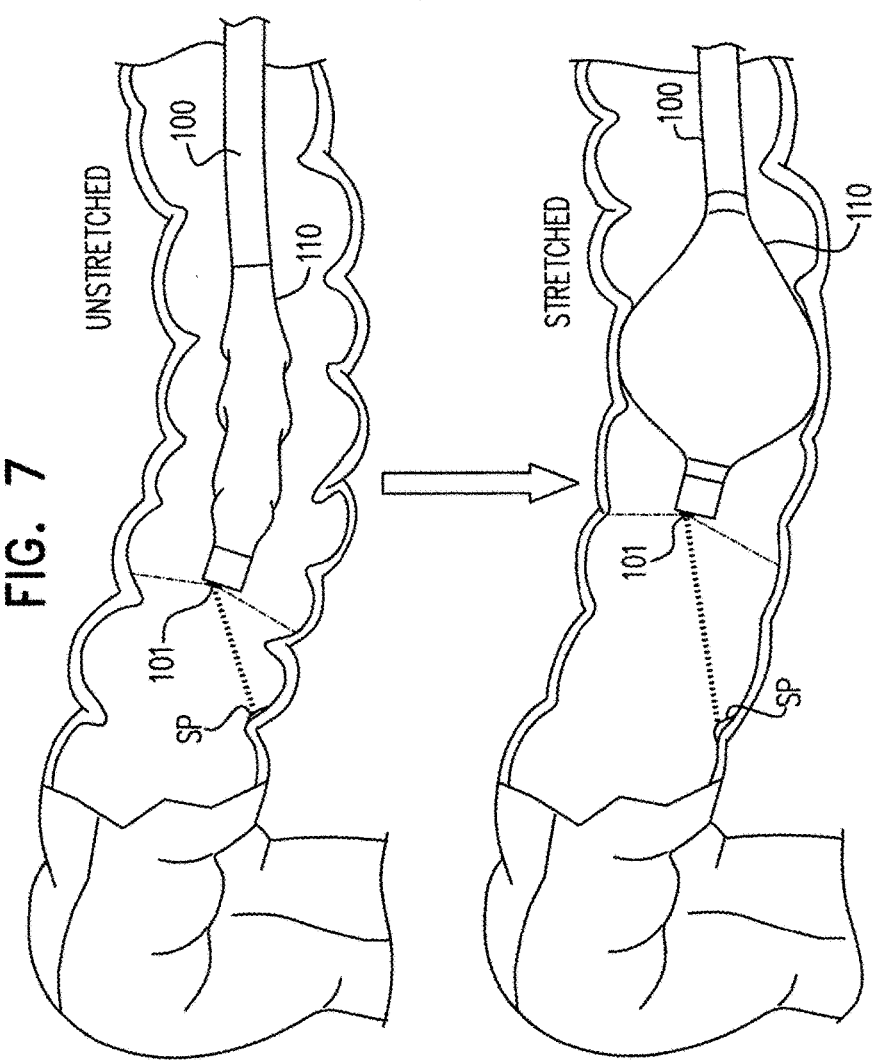

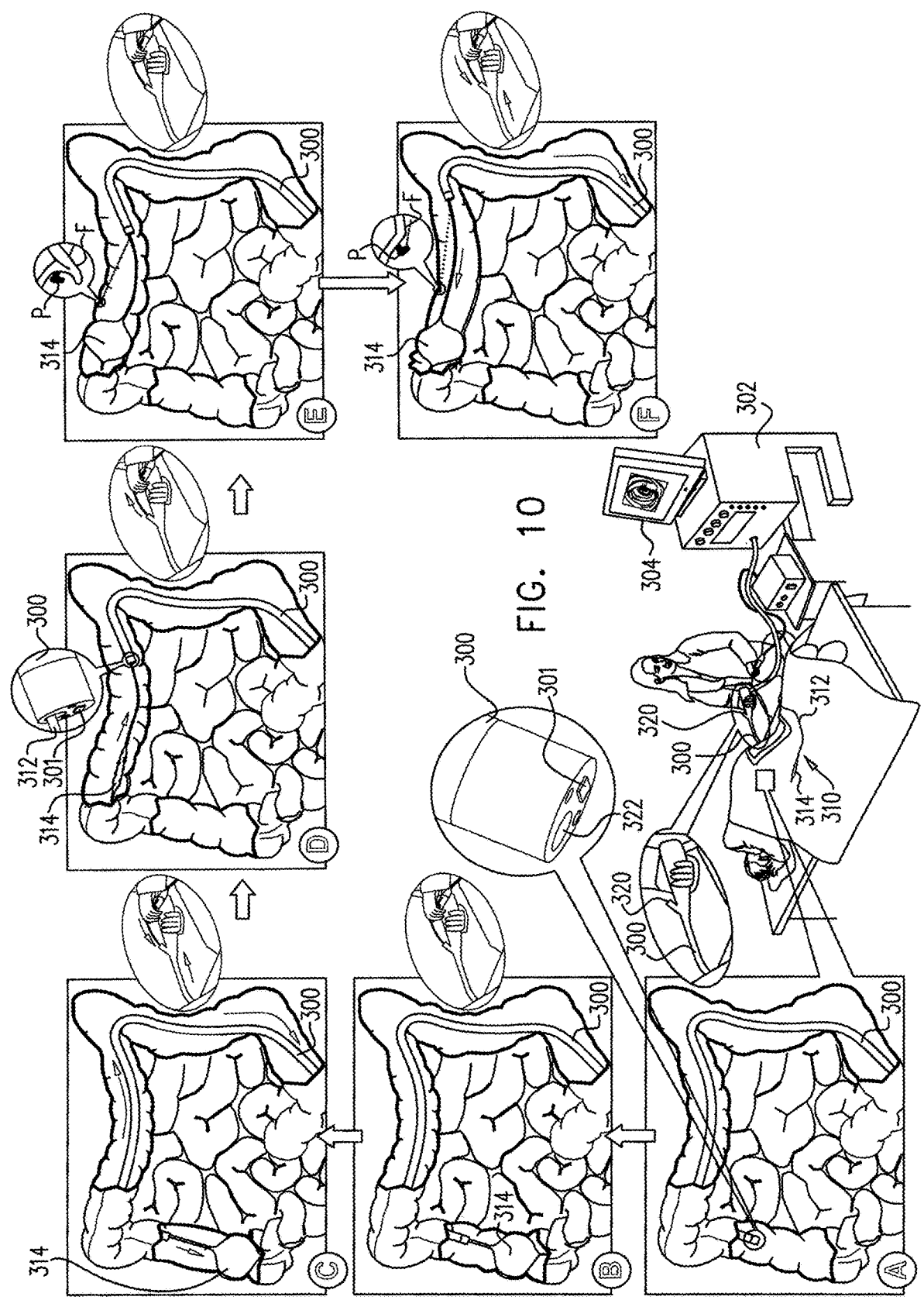

BALLOON-EQUIPPED ENDOSCOPIC DEVICES AND METHODS THEREOF

REFERENCE TO RELATED APPLICATIONS

The present application is a continuation of U.S. application Ser. No. 14/003,799, filed Dec. 15, 2013 and entitled "Balloon endoscope and methods of manufacture and use thereof" which is a national phase application of PCT Pat. App. No. PCT/IL2012/000003 which was filed Jan. 5, 2012 and which claims priority to U.S. Provisional Patent Application Ser. No. 61/457,351, filed Mar. 7, 2011 and entitled "Method of performing controlled withdrawal of an endoscope using a balloon endoscopic tool." The aforementioned disclosures are hereby incorporated by reference and priority is hereby claimed pursuant to 37 CFR 1.78(a)(4) and (5)(i).

Reference is also made to applicant's Published PCT Patent Applications WO2005/074377; WO2007/017854; WO2007/135665; WO2008/004228; WO2008/142685; WO2009/122395; WO2010/046891; WO2010/137025; and WO2011/111040, the disclosures of which are hereby incorporated by reference.

FIELD OF THE INVENTION

The present invention relates to endoscopy generally and more particularly to balloon endoscopes.

BACKGROUND OF THE INVENTION

The following patent publications and commercially available products are believed to represent the current state of the art: U.S. Pat. Nos. 3,837,347; 4,040,413; 4,148,307; 4,176,662; 4,195,637; 4,261,339; 4,453,545; 4,616,652; 4,676,228; 4,862,874; 4,917,088; 5,135,487; 5,259,366; 5,593,419; 6,007,482; 6,461,294; 6,585,639; 6,663,589; and 6,702,735; U.S. Patent Application publication Nos. 2003/0244361; 2004/0102681; 2005/0124856; 2005/0125005; 2005/0133453; 2005/0137457; 2005/0165233; 2005/0165273; 2005/0171400; 2006/0111610; and 2006/0161044; Japanese Patent Application publication No. JP2003-250896; Published PCT Patent Applications WO 2005/074377; WO 2005/017854; WO 2007/135665; WO 2008/004228; WO 2008/142685; WO 2009/122395; WO 2010/046891; WO 2010/137025; WO 2011/111040; and Double Balloon Endoscope product, including EC-450BI5 colonoscope, TS-13101 overtube and BS-2 front balloon, which interface with balloon pump controller BP-20 and EPX-4400HD video system, all commercially available from Fujinon Inc., of 10 High Point Drive, Wayne, N.J., USA.

SUMMARY OF THE INVENTION

The present invention seek to provide an improved balloon endoscope and improved methods for inflation of endoscope balloons and endoscope tool balloons and improved method for endoscope examinations.

There is thus provided in accordance with a preferred embodiment of the present invention an endoscopy system including a balloon-equipped endoscope including a balloon which is configured for slidable frictional engagement with an interior wall of a body passageway and axial stretching of the interior wall when inflated to a slidable frictional engagement pressure and displaced axially along the body passageway and a balloon inflation subsystem operative to selectably inflate the balloon to the slidable frictional engagement pressure.

Preferably, the endoscopy system also includes visual inspection functionality operative for visual inspection of the interior wall when axially stretched. In accordance with a preferred embodiment of the present invention the balloon-equipped endoscope is operative for visual inspection of the interior wall when axially stretched.

Preferably, the balloon inflation subsystem is operative to selectably inflate the balloon to an anchoring pressure within a predetermined range of anchoring pressures, different from the slidable frictional engagement pressure. In accordance with a preferred embodiment of the present invention the anchoring pressure is at least 60 millibar. Additionally or alternatively, the ratio between the anchoring pressure and the slidable frictional engagement pressure is in a range of 1.3-7.

In accordance with a preferred embodiment of the present invention the balloon inflation subsystem is operative for manual switching between the anchoring pressure and the slidable frictional engagement pressure at any time during operation thereof.

Preferably, the slidable frictional engagement pressure is not higher than 35 millibar. In accordance with a preferred embodiment of the present invention the slidable frictional engagement pressure is selected to cause the balloon, when inflated and displaced, to at least partially unfold natural folds of the interior wall.

Preferably, the slidable frictional engagement pressure is selected to cause the balloon, when inflated and displaced, to enhance visual contrast between polyps and other potential and actual pathologies and the interior wall.

In accordance with a preferred embodiment of the present invention the balloon-equipped endoscope and the balloon inflation subsystem are operative to enable systematic visual inspection of the body passageway while each portion of the body passageway being inspected is in a stretched state. Preferably, the balloon is configured for generally circumferentially uniform slidable frictional engagement with the interior wall.

In accordance with a preferred embodiment of the present invention the slidable frictional engagement pressure is manually selectable from multiple selectable slidable frictional engagement pressure states. Additionally or alternatively, the slidable frictional engagement pressure is automatically selectable from multiple selectable slidable frictional engagement pressure states.

Preferably, the multiple selectable slidable frictional engagement pressure states include at least three slidable frictional engagement pressure states in corresponding pressure ranges of 3-15 millibar, 15-23 millibar and 23-35 millibar. In accordance with a preferred embodiment of the present invention the balloon inflation subsystem is operative for manual switching between the multiple selectable slidable frictional engagement pressure states at any time during operation thereof.

Preferably, the endoscopy system also includes a gas reservoir in inflation propinquity to the balloon, adapted to provide inflation pressure buffering for the balloon. Additionally, the gas reservoir includes at least one of an interior volume of the balloon-equipped endoscope and an air reservoir. Additionally or alternatively, the gas reservoir has a selectable volume. Additionally, the selectable volume of the gas reservoir is variable in the range of 0-900 cc.

In accordance with a preferred embodiment of the present invention the balloon is configured to have an inflated balloon volume which is less than one third of the volume of the gas reservoir.

Preferably, the balloon is made of polyurethane type Elastollan 1185A.

In accordance with a preferred embodiment of the present invention an outer surface of the balloon is configured for enhanced slidable frictional engagement with the body passageway.

Preferably, the balloon inflation subsystem is operative for inflation of the balloon in an open-loop inflation sequence.

In accordance with a preferred embodiment of the present invention the body passageway includes at least one of a large intestine, a small intestine and an esophagus of a patient.

In accordance with a preferred embodiment of the present invention the balloon inflation subsystem is operative to automatically maintain inflation of the balloon at the slidable frictional engagement pressure at various balloon locations along the length of the body passageway, notwithstanding variations in the cross sectional area of the body passageway at such locations. Preferably, the slidable frictional engagement pressure is set within a predetermined pressure range configured to provide axial stretching of at least 35% of the interior wall. More preferably, the slidable frictional engagement pressure is set within a predetermined pressure range configured to provide axial stretching of at least 60% of the interior wall.

There is also provided in accordance with another preferred embodiment of the present invention an endoscopy method including the steps of displacing a balloon-equipped endoscope in slidable frictional engagement with an interior wall of a body passageway thereby producing axial stretching of the interior wall and visually inspecting the interior wall while it is axially stretched.

Preferably, the endoscopy method also includes, prior to the displacing step, inflating a balloon of the balloon-equipped endo scope to a slidable frictional engagement pressure. Additionally or alternatively, the endoscopy method also includes the step of deflating a balloon of the balloon-equipped endoscope.

In accordance with a preferred embodiment of the present invention the displacing a balloon-equipped endoscope includes pulling the balloon-equipped endoscope through at least a portion of the body passageway.

Preferably, the endoscopy method also includes the step of axially displacing the balloon-equipped endoscope in the body passageway with the balloon in a deflated state. In accordance with a preferred embodiment of the present invention the producing axial stretching of the interior wall includes at least partially unfolding natural folds of the interior wall. Preferably, the producing axial stretching of the interior wall includes enhancing visual contrast between polyps and other potential and actual pathologies and the interior wall.

In accordance with a preferred embodiment of the present invention the displacing a balloon-equipped endoscope in slidable frictional engagement with an interior wall of a body passageway includes at least partially removing materials and fluids in the body passageway from the interior wall prior to visual inspection thereof.

Preferably, the endoscopy method also includes inflating the balloon to an anchoring pressure within a predetermined range of anchoring pressures higher than the slidable frictional engagement pressure. Additionally, the endoscopy method also includes manual switching between the anchoring pressure and the slidable frictional engagement pressure at any time during examination of the body passageway.

In accordance with a preferred embodiment of the present invention the visually inspecting the interior wall while it is axially stretched includes systematically visually inspecting the body passageway while each portion of the body passageway being inspected is in a stretched state.

Preferably, the balloon is configured for generally circumferentially uniform slidable frictional engagement with an interior wall of a body passageway, thereby producing generally circumferentially uniform axial stretching of the interior wall.

In accordance with a preferred embodiment of the present invention the endoscopy method also includes the step of selecting the slidable frictional engagement pressure from multiple selectable slidable frictional engagement pressure states. Additionally, the endoscopy method also includes the step of switching between the multiple selectable slidable frictional engagement pressure states at any time during examination of the body passageway.

Preferably, the inflating comprises employing a gas reservoir in inflation propinquity to the balloon thereby providing inflation pressure buffering for the balloon. Additionally, the employing the gas reservoir includes employing at least one of an interior volume of the balloon-equipped endoscope and an air reservoir. Additionally or alternatively, the endoscopy method also includes the step of selecting a volume of the gas reservoir.

Preferably, the endoscopy method also includes providing a balloon inflation subsystem operative for inflating a balloon of the balloon-equipped endoscope to a slidable frictional engagement pressure and inflating the balloon at the slidable frictional engagement pressure by the balloon inflation subsystem in an open-loop inflation sequence.

In accordance with a preferred embodiment of the present invention the endoscopy method also includes providing a balloon inflation subsystem operative for inflating a balloon of the balloon-equipped endoscope to a slidable frictional engagement pressure, inflating the balloon at a slidable frictional engagement pressure by the balloon inflation subsystem and operating the balloon inflation subsystem to automatically maintain inflation of the balloon at the slidable frictional engagement pressure notwithstanding variations in the cross sectional area of the body passageway along its length.

Preferably, the body passageway includes at least one of a large intestine, a small intestine and an esophagus of a patient.

Preferably, the axial stretching of the interior wall includes axial stretching of at least 35% of the interior wall. More preferably, the axial stretching of the interior wall includes axial stretching of at least 60% of the interior wall.

There is further provided in accordance with yet another preferred embodiment of the present invention a multiple use balloon-equipped endoscopy system including an endoscope, a balloon permanently mounted on the endoscope, the balloon being configured and mounted on the endoscope for multiple uses and reprocessing between ones of such multiple uses, without balloon replacement and a balloon inflation subsystem operative to selectably inflate the balloon.

Preferably, the balloon includes a forward end portion and a rearward end portion and the forward end portion and the rearward end portion are mounted over rigid mounting elements of the endoscope. Additionally, at least one of the rigid mounting elements is a rigid collar element of the endoscope. Additionally or alternatively, at least one of the rigid mounting elements is a rigid tip portion of the endoscope.

In accordance with a preferred embodiment of the present invention the balloon-equipped endoscope includes a tubular sealing bending rubber sheath at a forward portion thereof and the length of the balloon is approximately equal to the length of the tubular sealing bending rubber sheath and aligned therewith.

Preferably, the balloon is made of polyurethane type Elastollan 1185A. Additionally or alternatively, the balloon has a thickness in the range of 20-35 micron.

In accordance with a preferred embodiment of the present invention the balloon-equipped endoscope is configured for withstanding over 100 conventional reprocessing cycles without the need to replace the balloon. More preferably, the balloon-equipped endoscope is configured for withstanding over 1,200 conventional reprocessing cycles without the need to replace the balloon. In accordance with a preferred embodiment of the present invention the balloon-equipped endoscope is configured for repeated use thereof for a period of at least five years without the need to replace the balloon.

There is even further provided in accordance with still another preferred embodiment of the present invention a multiple use balloon endoscopy method including providing an endoscope having a balloon mounted thereon in a manner that a resulting balloon-equipped endoscope is suitable for multiple endoscopy procedures, carrying out multiple endoscopy procedures employing the endoscope having the balloon mounted thereon and reprocessing the endoscope having the balloon mounted thereon between ones of such multiple endoscopy procedures, without balloon replacement.

Preferably, the carrying out multiple endoscopy procedures includes carrying out at least 100 endoscopy procedures. More preferably, the carrying out multiple endoscopy procedures includes carrying out at least 500 endoscopy procedures. Even more preferably, the carrying out multiple endoscopy procedures includes carrying out at least 1,200 endoscopy procedures. Most preferably, the carrying out multiple endoscopy procedures includes carrying out at least 3,600 endoscopy procedures.

There is yet further provided in accordance with another preferred embodiment of the present invention a systematic axial stretching endoscopy system including a balloon-equipped endoscope including a balloon which is configured for slidable frictional engagement with an interior wall of a body passageway and systematic axial stretching of the interior wall substantially along its entire length, when inflated to a slidable frictional engagement pressure and displaced axially along the body passageway and a balloon inflation subsystem operative to automatically maintain inflation of the balloon at the slidable frictional engagement pressure notwithstanding variations in the cross sectional area of the body passageway along its length.

Preferably, the systematic axial stretching endoscopy system also includes visual inspection functionality operative for visual inspection of the interior wall when it is axially stretched.

In accordance with a preferred embodiment of the present invention the balloon-equipped endoscope is operative for systematic visual inspection of the interior wall when it is axially stretched.

Preferably, the balloon inflation subsystem is operative to selectably inflate the balloon to an anchoring pressure within a predetermined range of anchoring pressures, different from the slidable frictional engagement pressure. Additionally, the ratio between the anchoring pressure and the slidable frictional engagement pressure is in the range of 1.3-7.

Preferably, the slidable frictional engagement pressure is not higher than 35 millibar. Additionally or alternatively, the slidable frictional engagement pressure is configured such that inflation and displacement of the balloon at least partially unfolds natural folds of the interior wall. Alternatively or additionally, the slidable frictional engagement pressure is configured such that inflation and displacement of the balloon is operative to enhance visual contrast between polyps and other potential and actual pathologies and the interior wall.

In accordance with a preferred embodiment of the present invention the balloon is configured for generally circumferentially uniform slidable frictional engagement with the interior wall. Additionally or alternatively, the slidable frictional engagement pressure is selectable from multiple selectable slidable frictional engagement pressure states.

Preferably, the balloon inflation subsystem is operative for manual switching between the multiple slidable frictional engagement pressure states at any time during operation thereof.

In accordance with a preferred embodiment of the present invention the systematic axial stretching endoscopy system also includes a gas reservoir in inflation propinquity to the balloon, adapted to provide inflation pressure buffering for the balloon. Additionally, the gas reservoir includes at least one of an interior volume of the balloon-equipped endoscope and an air reservoir. Additionally or alternatively, the balloon is configured to have an inflated balloon volume which is less than one third of the volume of the gas reservoir.

In accordance with a preferred embodiment of the present invention the balloon inflation subsystem is operative for inflation of the balloon in an open-loop inflation sequence.

In accordance with a preferred embodiment of the present invention, the balloon is inflatable and displaceable within at least one of a large intestine, a small intestine and an esophagus of a patient for providing desired stretching thereof.

Preferably, the slidable frictional engagement pressure is set within a predetermined pressure range selected to provide axial stretching of at least 35% of the interior wall. More preferably, the slidable frictional engagement pressure is set within a • predetermined pressure range selected to provide axial stretching of at least 60% of the interior wall.

There is also provided in accordance with yet another preferred embodiment of the present invention an endoscopy method including the steps of systematically displacing a balloon-equipped endoscope in slidable frictional engagement with an interior wall of a body passageway thereby producing axial stretching of the interior wall substantially along the entire length of the body passageway and visually inspecting substantially all of the interior wall while it is axially stretched.

Preferably, the endoscopy method also includes, prior to the displacing step, inflating a balloon of the balloon-equipped endo scope to a slidable frictional engagement pressure. Additionally or alternatively, the inflating includes employing a gas reservoir in inflation propinquity to the balloon thereby providing inflation pressure buffering for the balloon.

Preferably, the endoscopy method according also includes automatically maintaining inflation of the balloon at the slidable frictional engagement pressure notwithstanding variations in the cross sectional area of the body passageway along its length. Additionally or alternatively, the endoscopy method also includes the step of deflating the balloon of the balloon-equipped endoscope.

In accordance with a preferred embodiment of the present invention, the systematically displacing a balloon-equipped endoscope includes systematically pulling the balloon-equipped endoscope. Additionally or alternatively, the endoscopy method also includes the step of axially displacing the balloon-equipped endoscope in the body passageway with the balloon in a deflated state.

Preferably, the producing axial stretching of the interior wall includes at least partially unfolding natural folds of the interior wall. Additionally or alternatively, the producing axial stretching of the interior wall includes enhancing visual contrast between polyps and other potential and actual pathologies and the interior wall.

In accordance with a preferred embodiment of the present invention, the displacing a balloon-equipped endoscope in slidable frictional engagement with an interior wall of a body passageway includes at least partially removing materials and fluids in the body passageway from the interior wall which is visually inspected.

Preferably, the endoscopy method also includes inflating the balloon to an anchoring pressure within a predetermined range of anchoring pressures higher than the slidable frictional engagement pressure.

In accordance with a preferred embodiment of the present invention, the balloon is configured for generally circumferentially uniform slidable frictional engagement with the interior wall, thereby producing generally circumferentially uniform axial stretching of the interior wall.

Preferably, the endoscopy method also includes providing a balloon inflation subsystem operative for inflating a balloon of the balloon-equipped endoscope to a slidable frictional engagement pressure and inflating the balloon at a slidable frictional engagement pressure by the balloon inflation subsystem in an open-loop inflation sequence. Alternatively, the endoscopy method also includes providing a balloon inflation subsystem operative for inflating a balloon of the balloon-equipped endoscope to a slidable frictional engagement pressure, inflating the balloon at a slidable frictional engagement pressure by the balloon inflation subsystem and operating the balloon inflation subsystem to automatically maintain inflation of the balloon at the slidable frictional engagement pressure notwithstanding variations in the cross sectional area of the body passageway along its length.

Preferably, the body passageway includes at least one of a large intestine, a small intestine and an esophagus of a patient.

There is further provided in accordance with still another preferred embodiment of the present invention an endoscopy method including the steps of anchoring a balloon-equipped endoscope tool in engagement with an interior wall of a body passageway, forwardly displacing the balloon-equipped endoscope tool in anchoring engagement with the interior wall of the body passageway, thereby producing axial stretching of the interior wall of the body passageway and visually inspecting the interior wall while it is axially stretched.

Preferably, the anchoring a balloon-equipped endoscope tool in engagement with an interior wall of a body passageway includes inflating a balloon of the balloon-equipped endoscope tool to an anchoring pressure in the body passageway. Additionally, the visually inspecting the interior wall while it is axially stretched employs an endoscope.

In accordance with a preferred embodiment of the present invention, the endoscopy method also includes the steps of inserting the balloon-equipped endoscope tool through an instrument channel of the endoscope and positioning the balloon-equipped endoscope tool forwardly of the endoscope. Additionally or alternatively, the endoscopy method also includes, while forwardly displacing the balloon-equipped endoscope tool in anchoring engagement with the interior wall of the body passageway, retracting the endoscope in the body passageway.

In accordance with a preferred embodiment of the present invention, the endoscopy method also includes repeatedly performing multiple times the steps of positioning a balloon of the balloon-equipped endoscope tool forwardly of a forward end of the endoscope, inflating and thus anchoring the balloon in the body passageway, thereafter pushing the balloon-equipped endoscope tool forwardly, thereby stretching the body passageway to enable enhanced viewing of the interior of the body passageway with reduced folds and visually inspecting the stretched portion of the body passageway.

Preferably, the endoscopy method also includes the step of deflating a balloon of the balloon-equipped endoscope tool. Additionally or alternatively, the endoscopy method also includes the step of pulling the balloon-equipped endoscope tool rearwardly in the body passageway.

Preferably, the producing axial stretching of the interior wall includes at least partially unfolding natural folds of the interior wall. Additionally or alternatively, the producing axial stretching of the interior wall includes enhancing visual contrast between polyps and other potential and actual pathologies and the interior wall.

In accordance with a preferred embodiment of the present invention, the balloon-equipped endoscope tool is configured for systematically visually inspecting the body passageway while each portion of the body passageway being inspected is in a stretched state.

Preferably, the balloon is inflated in an open-loop inflation sequence. In accordance with a preferred embodiment of the present invention, the body passageway includes at least one of a large intestine, a small intestine and an esophagus of a patient.

In accordance with a preferred embodiment of the present invention, the axial stretching of the interior wall includes axial stretching of at least 35% of the interior wall. More preferably, the axial stretching of the interior wall includes axial stretching of at least 60% of the interior wall.

There is yet further provided in accordance with another preferred embodiment of the present invention an axial stretching endoscopy system including a balloon-equipped endoscope including a balloon which is configured for generally circumferentially uniform slidable frictional engagement with an interior wall of a body passageway and axial stretching of the interior wall substantially along its entire length, when inflated to a generally circumferentially uniform slidable frictional engagement pressure and displaced axially along the body passageway and a balloon inflation subsystem operative to selectably inflate the balloon to the generally circumferentially uniform slidable frictional engagement pressure.

Preferably, the balloon-equipped endoscope is operative for visual inspection of the interior wall when axially stretched. Additionally or alternatively, the balloon inflation subsystem is operative to selectably inflate the balloon to an anchoring pressure within a predetermined range of anchoring pressures, different from the slidable frictional engagement pressure.

In accordance with a preferred embodiment of the present invention, the generally circumferentially uniform slidable frictional engagement pressure is not higher than 35 millibar.

Preferably, the generally circumferentially uniform slidable frictional engagement pressure is configured to at least partially unfold natural folds of the interior wall when stretched. Additionally or alternatively, the generally circumferentially uniform slidable frictional engagement pressure is configured to enhance visual contrast between polyps and other potential and actual pathologies and the interior wall when stretched.

In accordance with a preferred embodiment of the present invention, the generally circumferentially uniform slidable frictional engagement pressure is configured to at least partially remove materials and fluids in the body passageway from the interior wall prior to visual inspection thereof.

Preferably, the axial stretching endoscopy system also includes a gas reservoir in inflation propinquity to the balloon, adapted to provide inflation pressure buffering for the balloon. Preferably, the balloon is made of polyurethane type Elastollan 1185A. Additionally or alternatively, the balloon has a thickness in the range of 20-35 micron.

In accordance with a preferred embodiment of the present invention, the balloon inflation subsystem is operative to selectably inflate the balloon within at least one of a large intestine, a small intestine and an esophagus of a patient. Additionally or alternatively, the balloon inflation subsystem is operative to automatically maintain inflation of the balloon at the generally circumferentially uniform slidable frictional engagement pressure notwithstanding variations in the cross sectional area of the body passageway along its length.

There is even further provided in accordance with yet another preferred embodiment of the present invention a balloon inflation/deflation system for use with an endoscope and including balloon inflation functionality providing a predetermined open-loop inflation sequence and balloon deflation functionality.

Preferably, the balloon inflation functionality is operative to inflate a balloon of a balloon-equipped endoscopic device in engagement with an interior wall of a body passageway under inspection to at least one of an anchoring pressure and a slidable frictional engagement pressure.

In accordance with a preferred embodiment of the present invention, the balloon inflation/deflation system also includes an inflated balloon pressure indicator, and the open loop inflation sequence includes an automatic inflation sequence, which includes at least one step of balloon inflation over a predetermined time duration, notwithstanding the exceedance of a preset inflated balloon pressure by the pressure measured in the inflated balloon pressure indicator.

Preferably, the balloon inflation predetermined time duration is short enough to prevent over-inflation in the inflated balloon and resulting potential damage to the body passageway under inspection. Additionally or alternatively, the balloon inflation functionality is configured to record a pressure decrease time duration between the end of the balloon inflation predetermined time duration and an indication by a pressure indicator that the pressure thereat is below a predetermined threshold.

Preferably, the predetermined open-loop inflation sequence is configured to provide an inflation duty cycle, defined as the ratio of the balloon inflation predetermined time duration to the pressure decrease time duration, which is at least 2. More preferably, the predetermined open-loop inflation sequence is configured to provide an inflation duty cycle, defined as the ratio of the balloon inflation predetermined time duration to the pressure decrease time duration, which is at least 5.

There is yet further provided in accordance with still another preferred embodiment of the present invention an endoscopy method including the steps of inflating a balloon of a balloon-equipped endoscopic device in engagement with an interior wall of a body passageway by an open-loop inflation sequence and deflating the balloon-equipped endoscopic device.

Preferably, the inflating the balloon by the open-loop inflation sequence includes performing an automatic inflation sequence, including at least one step of inflating the balloon over a predetermined time duration, notwithstanding the exceedance of a preset inflated balloon pressure by the pressure measured in an inflated balloon pressure indicator.

There is even further provided in accordance with yet another preferred embodiment of the present invention a balloon inflation/deflation system for use with an endoscope and including balloon anchoring functionality. providing inflation of a balloon to an anchoring pressure within a predetermined range of anchoring pressures and balloon slidable frictional engagement functionality providing inflation of the balloon to at least one slidable frictional engagement pressure within a predetermined range of slidable frictional engagement pressures, different from the predetermined range of anchoring pressures.

Preferably, the anchoring pressure is at least 60 millibar. Additionally or alternatively, the ratio between the anchoring pressure and the slidable frictional engagement pressure is in the range of 1.3-7.

In accordance with a preferred embodiment of the present invention, the balloon inflation/deflation system is also operative for manual switching between the anchoring pressure and the slidable frictional engagement pressure at any time during operation thereof.

Preferably, the slidable frictional engagement pressure is not higher than 35 millibar. Additionally or alternatively, the slidable frictional engagement pressure is manually selectable within the predetermined range of slidable frictional engagement pressures.

In accordance with a preferred embodiment of the present invention, at least one of the balloon anchoring functionality and balloon slidable frictional engagement functionality is operative for inflation of the balloon in an open-loop inflation sequence. Additionally or alternatively, at least one of the balloon anchoring functionality and balloon slidable frictional engagement functionality is operative to automatically maintain inflation of the balloon at the respective anchoring pressure or slidable frictional engagement pressure, notwithstanding variations in a cross sectional area along the length of a body passageway in which the balloon is at inflation engagement.

There is also provided in accordance with yet another preferred embodiment of the present invention a balloon for use in a balloon-equipped endoscope, the balloon including a central portion and first and second end portions, the balloon being characterized by at least one of the central portion having a frictional engagement enhancing outer facing surface configuration, stretchability of the balloon being a nonlinear function of internal pressure applied to the interior of the balloon and the first and second end portions having lengths which are at least approximately twice their internal radii.

Preferably, the frictional engagement enhancing outer facing surface configuration of the balloon includes frictional engagement enhancing ridges. Additionally or alternatively, the frictional engagement enhancing outer facing surface configuration of the balloon includes a high friction coating.

In accordance with a preferred embodiment of the present invention, the balloon is relatively not stretchable under relatively low operative internal pressures and is relatively stretchable under relatively high operative internal pressures.

There is further provided in accordance with still another preferred embodiment of the present invention a balloon mounted on an endoscope, the balloon including a central portion and first and second end portions, the balloon being characterized by at least one of the central portion having a frictional engagement enhancing outer facing surface configuration, stretchability of the balloon being a nonlinear function of internal pressure applied to the interior of the balloon, the first and second end portions having lengths which are at least approximately twice their internal radii, the overall end-to-end length of the balloon being at least equal to the overall length of an underlying outwardly-facing surface of the endoscope when fully bent, the internal radii of the balloon each being less than 0.4 m larger than the exterior radius of the endoscope and the internal radii of the balloon each being between 0.2 and 0.75 larger than the exterior radius of the endoscope.

Preferably, the overall end to end length of the balloon is at least equal to the overall length of an underlying outwardly-facing surface of the endoscope when fully bent and the internal radii of the balloon are each between 0.2 mm and 0.75 mm larger than the exterior radius of the endoscope.

In accordance with a preferred embodiment of the present invention, the balloon is relatively not stretchable under relatively low operative internal pressures and is relatively stretchable under relatively high operative internal pressures.

Preferably, the slidable frictional engagement pressure is selected to cause the balloon, when inflated and displaced, to at least partially remove materials and fluids in the body passageway from the interior wall prior to visual inspection thereof.

There is further provided in accordance with yet another preferred embodiment of the present invention a multiple use balloon-equipped endoscopy system which includes an endoscope and rigid mounting elements, wherein at least one of the rigid mounting elements is a rigid collar element which is mounted on the endoscope. Preferably, the rigid collar element is crimp-mounted on the endoscope.

BRIEF DESCRIPTION OF THE DRAWINGS

The present invention will be understood and appreciated more fully from the following detailed description, taken in conjunction with the drawings in which:

FIGS. 2A and 2B are simplified illustrations of particular features of preferred embodiments of a balloon useful in the system and methodology of FIG. 1;

FIG. 7 is a simplified illustration of the transverse colon in unstretched and stretched states;

FIG. 8 is a simplified illustration of images produced on a monitor forming part of the system of FIG. 1 when viewing the transverse colon in the unstretched and stretched states of FIG. 7;

FIG. 10 is a simplified illustration of an endoscope system and methodology constructed and operative in accordance with another preferred embodiment of the present invention;

DETAILED DESCRIPTION OF PREFERRED EMBODIMENTS

Figure 1:
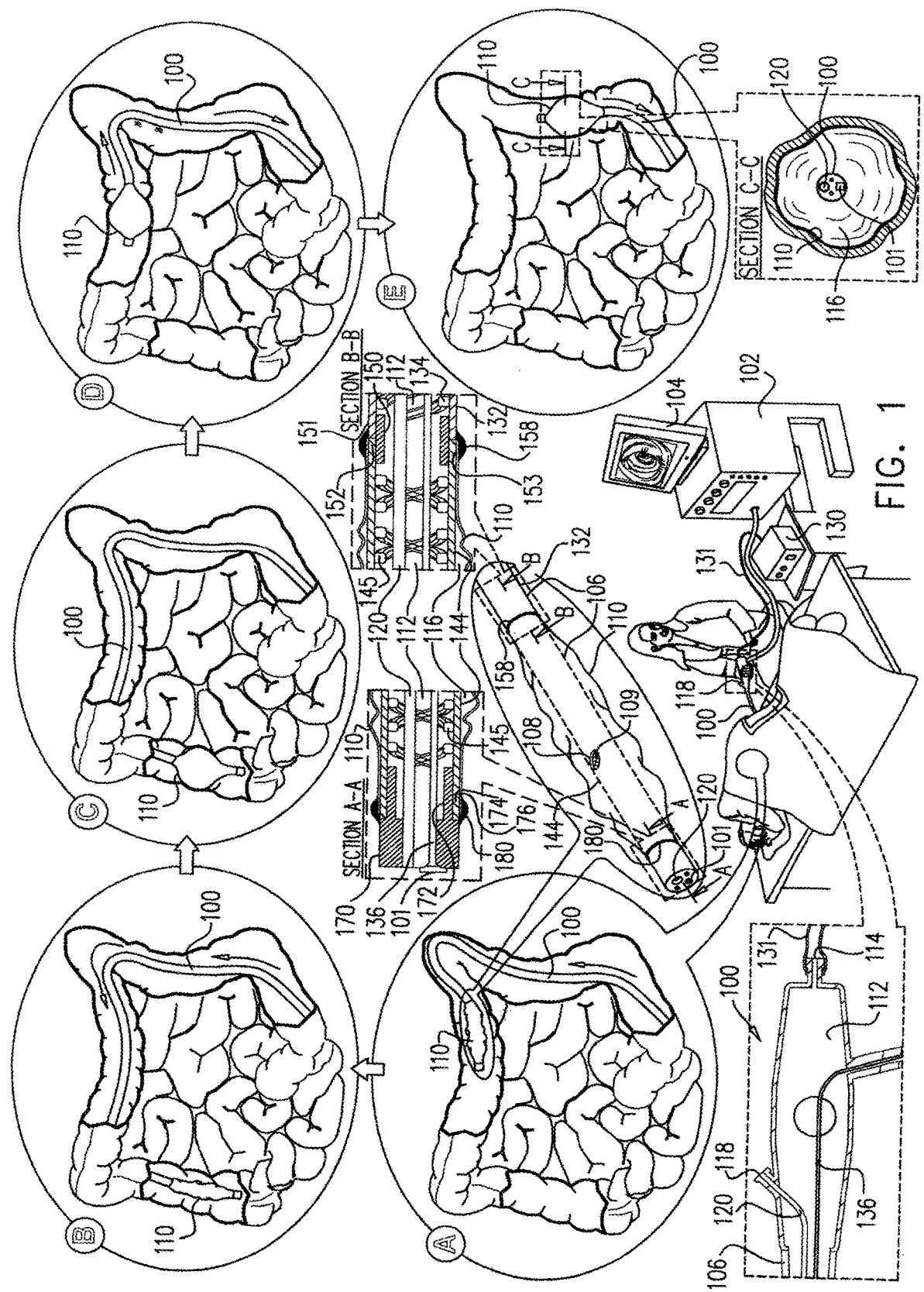
FIG. 1 is a simplified illustration of an endoscope system and methodology constructed and operative in accordance with a preferred embodiment of the present invention.

Reference is now made to FIG. 1, which is a simplified illustration of an endoscope system and methodology constructed and operative in accordance with a preferred embodiment of the present invention.

The terms "endoscope" and "endoscopy" are used throughout in a manner somewhat broader than their customary meaning and refer to apparatus and methods which operate within body cavities, passageways and the like, such as, for example, the small intestine and the large intestine. Although these terms normally refer to visual inspection, as used herein they are not limited to applications which employ visual inspection and refer as well to apparatus, systems and methods which need not necessarily involve visual inspection.

The term "forward" refers to the remote end of an endoscope, accessory or tool furthest from the operator or to a direction facing such remote end.

The term "rearward" refers to the end portion of an endoscope, accessory or tool closest to the operator, typically outside an organ or body portion of interest or to a direction facing such end portion.

Pressure is indicated in millibars above ambient (atmospheric) pressure.

FIG. 1 illustrates the general structure and operation of an embodiment of a balloon endoscope, constructed and operative in accordance with the present invention. As seen in FIG. 1, an endoscope 100, having a CCD 101 at a forward end thereof, is connected to an endoscope system 102 including a monitor 104. Alternatively, CCD 101 may be replaced by any other suitable detector.

Other than as specifically described hereinbelow, the endoscope 100 may be a conventional endoscope, such as an EC-3470LK video colonoscope or a VSB-3430K video enteroscope, the endoscope system 102 may be a conventional endoscope system, such as a console including a EPK-1000 video processor, and the monitor 104 may be a conventional monitor, such as a SONY LMD-2140MD medical grade flat panel LCD monitor, all commercially available from Pentax Europe GmbH, 104 Julius Vosseler St., 22527 Hamburg, Germany.

As distinct from a conventional endoscope, and as described in Published PCT Application WO 2011/111040, published on Sep. 15, 2011, the disclosure of which is hereby incorporated by reference, the endoscope 100 has an outer sheath 106 which is preferably provided with at least one balloon inflation/deflation aperture 108, with which is associated a fluid flow discriminator such as a filter 109, preferably a gas permeable, liquid impermeable filter. The aperture 108 preferably communicates with the interior of an inflatable/deflatable balloon 110, sealably mounted on outer sheath 106, and with an interior volume 112 of the endoscope 100, which in conventional endoscopes is sealed from the exterior other than via a leak test port 114 at a rearward portion of the endoscope. In accordance with a preferred embodiment of the present invention, interior volume 112 generally fills the interior of the endoscope 100 which is not occupied by conduits and other elements extending therethrough.

It is appreciated that a gas communication path extends between the leak test port 114 via the interior volume 112 of the endoscope, filter 109 and aperture 108 to a balloon volume 116 at the interior of inflatable/deflatable balloon 110. It is a particular feature of this embodiment of the present invention that the interior volume 112 provides a gas reservoir, enabling quick pressurization and depressurization of balloon 110 and a directly coupled pressure buffer operative to reduce the amplitude of pressure changes inside the balloon 110 resulting from corresponding changes in balloon volume 116. It is appreciated that having a gas reservoir, such as interior volume 112, in inflation propinquity to balloon 110 as described hereinabove, also provides inflation pressure buffering for balloon 110 and enables enhanced stability and accuracy to be achieved in the pressurization of the inflated balloon volume 116.

Preferably for certain applications, the balloon 110 is designed to have an inflated balloon volume 116 in the range of approximately 60-80 cc, when the balloon 110 is inflated to a pressure of 10 millibar, and the interior volume 112 of the endo scope has a volume in the range of approximately 450-550 cc.

Preferably for other applications, the balloon 110 is designed to have an inflated balloon volume 116 in the range of approximately 130-180 cc, when the balloon 110 is inflated to a pressure of 10 millibar, and the interior volume 112 of the endoscope has a volume in the range of approximately 700-900 cc.

Preferably for still other applications, the balloon 110 is designed to have an inflated balloon volume 116 in the range of approximately 100-150 cc, when the balloon 110 is inflated to a pressure of 10 millibar, and the interior volume 112 of the endoscope has a volume in the range of approximately 500-900 cc.

Balloon 110 preferably is configured to have an inflated balloon volume 116 which is less than half of interior volume 112 of the endoscope. More preferably, balloon 110 preferably is configured to have an inflated balloon volume 116 which is less than one third of interior volume 112 of the endoscope. Most preferably, balloon 110 preferably is configured to have an inflated balloon volume 116 which is less than one fifth of interior volume 112 of the endoscope.

It is a particular feature of an embodiment of the present invention, that inflatable balloon 110 is directly coupled to a gas reservoir, such as interior volume 112, having a volume typically 3-7 times higher than the inflated balloon volume 116.

Alternatively, depending on the configuration of the endoscope, the leak test port 114 need not be located as illustrated in FIG. 1 but may be at a different location. As a further alternative, the leak test port 114 need not be employed for this purpose and an additional port communicating with interior volume 112 may be employed.

Alternatively, as not shown, the interior of balloon 110 may communicate with a fluid flow passageway other than interior volume 112, such as, for example, a fluid conduit or other conduit, such as a conventional dedicated balloon inflation/deflation channel and aperture 108 and filter 109 may be obviated.

An instrument channel port 118 preferably communicates with an instrument channel 120, extending throughout the length of endoscope 100.

Inflatable/deflatable balloon 110 preferably is inflated and/or deflated via the interior volume 112 of the balloon endoscope 100 by a balloon inflation/deflation system 130, which constitutes a balloon inflation and/or deflation subsystem of the endoscopy system of FIG. 1. Balloon inflation/deflation system 130 is preferably connected to the leak test port 114 by an inflation/deflation tube 131.

Figure 2A:
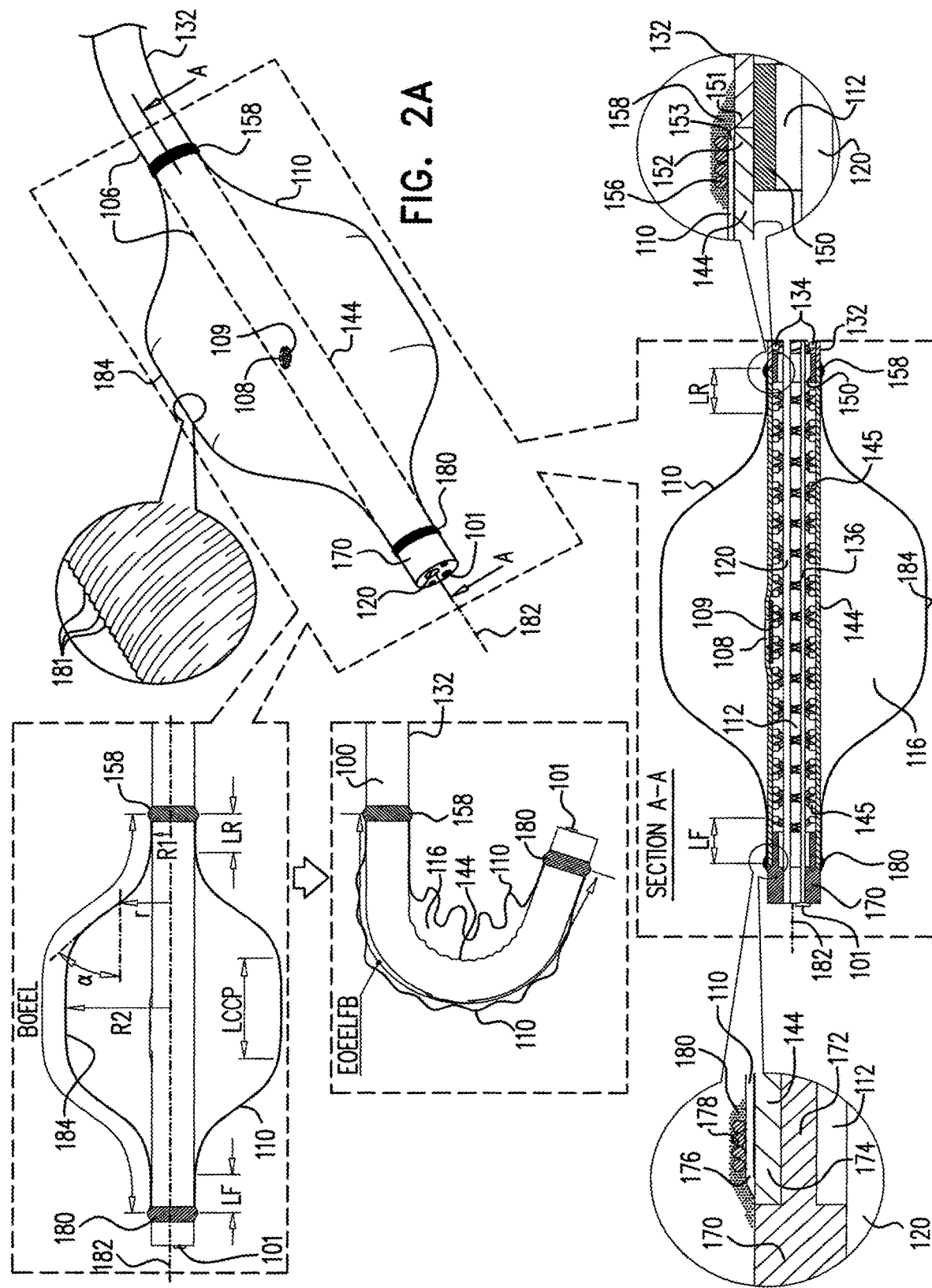

Reference is now made additionally to FIGS. 2A and 2B, which are simplified illustrations of particular features of preferred embodiments of a balloon useful in the system and methodology of FIG. 1.

As seen in FIG. 2A, balloon 110 is sealably mounted over a forward portion of endoscope 100, overlying outer sheath 106. Preferably, outer sheath 106 includes a tubular sealing sheath 132, overlying a reinforcement mesh 134, which serves to maintain the interior volume 112 of endoscope 100 against collapse during bending thereof. Instrument channel 120 and an optical bundle 136 extend inwardly of reinforcement mesh 134, through the interior volume 112 of endoscope 100. Optical bundle 136 is preferably coupled to CCD 101. Other conduits and other elements may also extend through this interior volume.

It is further appreciated that notwithstanding the fact that various conduits may extend through the interior volume 106, their presence does not result in fluid communication between the interior volume 112 and the interior of any conduit extending therethrough.

Forwardly of tubular sealing sheath 132, outer sheath 106 includes a tubular sealing bending rubber sheath 144, which also seals the interior volume 112 from the exterior of endoscope 100. Bending rubber sheath 144 may be an off-the-shelf product, such as a silicone bending rubber sheath part number SPRBSS11, PVC bending rubber sheath part number SPRBSP11, or a Viton bending rubber sheath part number SPRBSV11, all commercially available from Endoscope Repair Inc. of 5201 Blue Lagoon Drive, No. 815 Miami, Fla. 33126 USA. Preferably, aperture 108 is formed in sheath 144 and overlies filter 109. It is appreciated that plural apertures 108, having associated therewith plural filters 109, may be provided for gas communication between the interior of inflatable/deflatable balloon 110 and the interior volume 112 of endoscope 100. It is also appreciated that filter 109 may be obviated.

Bending rubber sheath 144 overlies a selectably bendable reinforcement mesh 145, which is selectably bendable in response to operator manipulation of steering knobs (not shown) at a rearward portion of endoscope 100, and protects the forward selectably bendable portion of endoscope 100 against collapse during bending thereof. Instrument channel 120 and optical bundle 136 and optionally other elements extend interiorly of selectably bendable reinforcement mesh 145, through the interior volume 112 of the endoscope.

In accordance with a preferred embodiment of the present invention, the forward end of reinforcement mesh 134 and the rearward end of selectably bendable reinforcement mesh 145 are joined together by a rigid collar element 150, preferably formed of metal or rigid plastic, which underlies a forward end 151 of tubular sealing sheath 132, which is butted against a rearward end 152 of sheath 144. A rearward end 153 of inflatable balloon 110 is retained over rearward end 152 of sheath 144 preferably by a wire 156 wound thereabout. The rearward end 153 of balloon 110 is preferably additionally sealed to respective ends 151 and 152 of sheaths 132 and 144 by an adhesive 158, such as a medical grade epoxy M31-CL, commercially available from Henkel Corporation, One Henkel Way, Rocky Hill, Conn. 06067, USA.

Further in accordance with a preferred embodiment of the present invention, endoscope 100 includes, at the forward end thereof, a rigid tip portion 170 which is connected to a forward end of selectably bendable reinforcement mesh 145. Preferably, rigid tip portion 170 is formed of metal or rigid plastic, and a rearward portion 172 thereof underlies a forward end 174 of sheath 144. A forward end 176 of inflatable balloon 110 is retained over forward end 174 of sheath 144 preferably by a wire 178 wound thereabout. The forward end 176 of balloon 110 is preferably additionally sealed to rigid tip portion 170 by an adhesive 180, such as a medical grade epoxy M31-CL, commercially available from Henkel Corporation.

Filter 109 is preferably mounted onto an inner surface of sheath 144 underlying aperture 108 by any suitable technique, such as by the use of adhesive, for example a Polychloroprene based Contact Cement commercially available from Elmer's Products Inc. of One Easton Oval, Columbus, Ohio 43219, USA. It is appreciated that a gas communication path extends between leak test port 114 via the interior volume 112, filter 109 and aperture 108 to balloon volume 116 at the interior of inflatable/deflatable balloon 110.

It is a particular feature of an embodiment of the present invention that the length of balloon 110 is approximately similar to the length of the bending rubber sheath 144 and aligned therewith, as shown in FIG. 2A. This arrangement allows rearward end 153 of balloon 110 to be mounted over rigid collar element 150, by wound wire 156 and adhesive 158, and allows forward end 176 of balloon 110 to be mounted over rearward portion 172 of rigid tip portion 170, by wound wire 178 and adhesive 180.

It is also a particular feature of an embodiment of the present invention that the rearward end 153 of balloon 110 is mounted over the rearward end 152 of sheath 144. It is additionally a particular feature of an embodiment of the present invention that the forward end 176 of balloon 110 is mounted over the forward end 174 of sheath 144.

It is a further particular feature of a preferred embodiment of the present invention that rearward end 153 of balloon 110 is mounted over rigid collar element 150 and over rearward end 152 of sheath 144 by wound wire 156 and adhesive 158 and that forward end 176 of balloon 110 is mounted over rearward portion 172 of rigid tip portion 170 and over forward end 174 of sheath 144 by wound wire 178 and adhesive 180.

The aforesaid arrangement has the advantage of providing secure and stable mounting of balloon 110 onto existing rigid mounting elements of the endo scope without the requirement of additional rigid mounting elements which could limit the flexibility of the endoscope. The resulting structure described above is both suitable for conventional reprocessing and provides a balloon-equipped endoscope which does not normally require balloon replacement.

It is a particular feature of the embodiments shown in FIGS. 2A and 2B that inflatable/deflatable balloon 110 is inflated and/or deflated via the interior volume 112 of the balloon endoscope 100. The available cross section of the interior volume 112 for inflation/deflation of the balloon 110 is typically 15-50 square millimeters, which is approximately 6-30 times greater than the cross section of balloon inflation channels employed in the prior art. The interior volume 112 of the endoscope thus functions as a gas reservoir directly coupled to the balloon volume 116 and enables inflation and deflation of the balloon 110 to take place significantly more efficiently than in prior art balloon endoscopes.

It is appreciated that the embodiments of FIGS. 2A and 2B enable retrofit of existing non-balloon endoscopes as balloon endoscopes, and eliminate complications and per-treatment costs associated with conventional external balloon devices. These complications include limitations on bendability, torqueability and maneuverability as well as increased cross-section and increased endoscope head resistance to advancement.

Prior art balloon endoscopes have relatively high complexity and per-treatment costs arising from required balloon mounting and reprocessing, such as required cleaning and disinfection of the inflation/deflation channel. Prior art single-use components employed in such endoscopes are also characterized by relatively high per-treatment costs. These embodiments of the present invention enable much of the aforesaid complexity and high per-treatment costs to be avoided.

In accordance with a preferred embodiment of the present invention and as also seen in FIGS. 2A and 2B, the configuration of inflatable/deflatable balloon 110 is generally characterized as follows: balloon 110 is preferably formed of polyurethane of thickness in the range of 10-75 micron, and more preferably in the range of 20-35 micron. It is a particular feature of the present invention that the stretchability of the balloon 110 is a non-linear function of the balloon internal pressure.

In accordance with a preferred embodiment of a balloon of the present invention, the balloon 110 is relatively not stretchable under low operative internal pressures and is relatively stretchable under high operative internal pressures. Preferably the balloon is not stretchable beyond 3% under relatively low internal pressures up to approximately 10 millibar and is stretchable beyond 30%-40% under relatively high internal pressures of approximately 60-80 millibar, respectively. An example of a balloon providing the aforementioned non-linear stretchability as function of balloon internal pressure is a balloon formed by blow-molding, having length of 110 millimeter and diameter of 48 millimeter when inflated to a pressure of 10 millibar, having wall thickness of 26-28 micron and made of polyurethane type Tecothane D-1055D, commercially available from Lubrizol Corporation of 29400 Lakeland Boulevard Wickliffe, Ohio, USA, with 1.2%-2.5% of Erucamide additive.

Alternative preferable materials of balloon 110 include other polyurethane formulae, nylon or silicon.

Preferably, the material, thickness and dimensions of balloon 110 are configured to minimize interference with endoscope performance parameters when balloon 110 is deflated, such as bendability and ease of advancement, while providing long-term usability of the balloon-equipped endoscope during repeated endoscopy procedures and conventional reprocessing cycles, without requiring replacement of balloon 110.

In accordance with a preferred embodiment of a balloon of the present invention, the balloon-equipped endoscope is capable of withstanding over 20 conventional reprocessing cycles without the need to replace the balloon.

In accordance with a more preferred embodiment of a balloon of the present invention, the balloon-equipped endoscope is capable of withstanding over 100 conventional reprocessing cycles without the need to replace the balloon.

In accordance with an even more preferred embodiment of a balloon of the present invention, the balloon-equipped endoscope is capable of withstanding over 500 conventional reprocessing cycles without the need to replace the balloon.

In accordance with a further preferred embodiment of a balloon of the present invention, the balloon-equipped endoscope is capable of withstanding over 1,200 conventional reprocessing cycles without the need to replace the balloon.

In accordance with a most preferred embodiment of a balloon of the present invention, the balloon-equipped endoscope is capable of withstanding over 3,600 conventional reprocessing cycles without the need to replace the balloon.

It is appreciated that for an average number of 60 endoscopy procedures and 60 corresponding conventional reprocessing cycles per month, this most preferred embodiment of a balloon-equipped endoscope can be used repeatedly for a period of at least five years without the need to replace the balloon.

An example of a balloon capable of withstanding over 1,200 conventional reprocessing cycles, and preferably 3,600 conventional reprocessing cycles and corresponding five years of operation without the need to replace the balloon, is a balloon having a wall thickness of 26 microns, a length of 110 millimeters and a diameter of 48 millimeters when inflated to a pressure of 10 millibar, formed by blow-molding and made of polyurethane type Elastollan 1185A, commercially available from BASF Corporation of Carl-Bosche Strasse 38, 67056 Ludwigshafen, Germany. This balloon was tested and successfully withstood over 1,200 cycles of conventional reprocessing, with an overall change in dimensions and mechanical parameters of less than 2%, and no noticeable decrease in wall thickness. If a 6% change in dimensions and mechanical parameters over the balloon lifetime is acceptable, this balloon is expected to withstand over 3,600 conventional reprocessing cycles and corresponding usage time period of 5 years without the need to normally replace the balloon in a balloon-equipped endoscope.

Preferably, the outer surface of balloon 110 is configured to define an array of multiple generally parallel ridges 181, which are preferably arranged to be generally perpendicular to a longitudinal axis of symmetry of the balloon, indicated by reference numeral 182 in FIGS. 2A and 2B. Any other suitable frictional engagement enhancing surface configuration of the balloon, useful for enhancing slidable frictional engagement between the balloon 110 and the interior surface of a tubular body portion sought to be stretched, may alternatively be employed. It is appreciated that balloon 110 may be formed of a relatively high friction material such as high-friction silicon, or alternatively the outer surface of balloon 110 may be coated with a high-friction coating.

Balloon 110 preferably has an overall length of 50-130 mm and more preferably 80-100 mm. Rearward and forward ends 153 and 176 respectively of balloon 110 are generally cylindrical and have a fixed inner cross-sectional radius R1, when forming part of balloon endoscope 100. R1 is preferably between 4 and 7 mm so as to tightly engage the adjacent portions of the endoscope.

It is a particular feature of the present invention that in accordance with a preferred embodiment of the present invention, R1 for a given balloon is between 0.2 mm and 0.75 mm larger than the exterior radius of the outer sheath 106 of the endoscope 100 onto which it is mounted. More preferably, R1 for a given balloon is no greater than 0.4 mm larger than the exterior radius of the outer sheath 106 of the endoscope 100 onto which it is mounted.

Preferably the respective lengths LR and LF (FIG. 2A) of rearward and forward ends 153 and 176 of balloon 110 are at least 5.5 mm. More preferably, the respective lengths LR and LF (FIG. 2A) of rearward and forward ends 153 and 176 of balloon 110 are in the range of 10-25 mm.

It is a particular feature of an embodiment of the present invention that the aforesaid relatively narrow spacing between the ends of the balloon and the sheath, namely that R1 for a given balloon is between 0.2 mm and 0.75 mm larger than the exterior radius of the outer sheath 106 of the endoscope 100 onto which it is mounted, is combined with the relatively large lengths of the ends of the balloon, as set forth in the preceding paragraph. It is appreciated that the aforementioned arrangement maintains bendability of the balloon-mounted endoscope, while reducing forces applied on the attachment locations of balloon 110 to endoscope 100, at wire 156 and adhesive 158, and at wire 178 and adhesive 180. It is further appreciated that force reduction on the attachment locations of balloon 110 to endoscope 100 increases the reusability of the balloon-equipped endoscope without the need to replace balloon 110.

A central cylindrical portion 184 of balloon 110 typically has a length LCCP (FIG. 2A) of 20-70 mm, and more preferably 25-55 mm, and has a fixed inner cross-sectional radius R2, when inflated to a nominal pressure, such as 5-10 millibars. R2 is preferably between 20 and 35 mm depending on the application.

Extending between the central cylindrical portion 184 and each of the rearward and forward ends 153 and 176 respectively are circularly symmetric tapered portions whose inner radius changes from R2 to R1 preferably in accordance with the following function:

$$\cos(\text{Alpha}) \geq r/R2$$

where r is the inner radius of the balloon at a given location between the central cylindrical portion 184 and one of ends 153 and 176; and Alpha is the angle between the tangent to the balloon at the given location and the longitudinal axis of symmetry 182 of the balloon (FIG. 2A).

More preferably, cos(Alpha) is approximately equal to r/R2.

It is appreciated that the foregoing balloon configuration is applicable not only to balloon endoscopes but also to balloon catheters and balloon-equipped endoscope tools, with suitable adjustment being made to R1 and R2.

It is a particular feature of the present invention that balloon 110 is generally non-stretchable at inflation pressure of 5-10 millibar. It is a further particular feature of the present invention that the overall end to end length of balloon 110, designated in FIG. 2A as BOEEL, is equal to or greater than the overall length of the underlying outwardly-facing surface of the outer sheath 106 of endoscope 100 when fully bent, designated in FIG. 2A as EOEELFB.

Alternatively other balloon configurations may be employed.

Reference is now made additionally to FIG. 2B, which is a simplified illustration of particular features of a preferred embodiment of a balloon useful in the system and methodology of FIG. 1 and is an alternative to the structure of FIG. 2A, described hereinabove. Those elements which are substantially identical in the embodiments of FIGS. 2A and 2B are designated by the same reference numerals. Preferably the features of the balloon 110 shown in FIG. 2A and described hereinabove are also present in the balloon 110 of FIG. 2B.

As seen in FIG. 2B, balloon 110 is sealably mounted over a forward portion of endoscope 100, overlying outer sheath 106. Preferably, outer sheath 106 includes a tubular sealing sheath 132, overlying a reinforcement mesh 134, which serves to maintain the interior volume of endoscope 100 against collapse during bending thereof. Instrument channel 120 and an optical bundle 136 extend inwardly of reinforcement mesh 134, through the interior volume 112 of endoscope 100. Optical bundle 136 is preferably coupled to CCD 101. Other conduits and other elements may also extend through this interior volume.

It is further appreciated that notwithstanding the fact that various conduits may extend through the interior volume 106, their presence does not result in fluid communication between the interior volume 112 and the interior of any conduit extending therethrough.

Forwardly of tubular sealing sheath 132, outer sheath 106 includes a tubular sealing bending rubber sheath 144, which also seals the interior volume 112 from the exterior of endoscope 100. Bending rubber sheath 144 may be an off-the-shelf product, such as a silicone bending rubber sheath part number SPRBSS11, PVC bending rubber sheath part number SPRBSP11, or a Viton bending rubber sheath part number SPRBSV11, all commercially available from Endoscope Repair Inc. Preferably, aperture 108 is formed in sheath 144 and overlies filter 109. It is appreciated that plural apertures 108, having associated therewith plural filters 109, may be provided for gas communication between the interior of inflatable/deflatable balloon 110 and the interior volume 112 of endoscope 100. It is also appreciated that filter 109 may be obviated.

Bending rubber sheath 144 overlies a selectably bendable reinforcement mesh 145, which is selectably bendable in response to operator manipulation of steering knobs (not shown) at a rearward portion of endoscope 100, and protects the forward selectably bendable portion of endoscope 100 against collapse during bending thereof. Instrument channel 120 and optical bundle 136 and optionally other elements extend interiorly of selectably bendable reinforcement mesh 145, through the interior volume 112 of the endoscope.

In accordance with a preferred embodiment of the present invention, the forward end of reinforcement mesh 134 and the rearward end of selectably bendable reinforcement mesh 145 are joined together by a rigid collar element 150, preferably formed of metal or rigid plastic, which underlies a forward end 151 of tubular sealing sheath 132, which is butted against a rearward end 152 of sheath 144. Rearward end 152 of sheath 144 is preferably retained over rigid collar element 150 by a wire wound thereabout, and is preferably additionally sealed to forward end 151 of tubular sealing sheath 132 by an adhesive 186, such as a medical grade epoxy M31-CL, commercially available from Henkel Corporation.

Also in the embodiment of FIG. 2B, endoscope 100 includes, at the forward end thereof, a rigid tip portion 170 which is connected to a forward end of selectably bendable reinforcement mesh 145. Preferably, rigid tip portion 170 is formed of metal or rigid plastic, and a rearward portion 172 thereof underlies a forward end 174 of sheath 144. Forward end 174 of sheath 144 is preferably retained over rearward portion 172 of rigid tip portion 170 by a wire wound thereabout, and is preferably additionally sealed to rigid tip portion 170 by an adhesive 188, such as a medical grade epoxy M31-CL, commercially available from Henkel Corporation.

In contrast to the structure shown in FIG. 2A, in the embodiment of FIG. 2B, a rearward end 153 of inflatable balloon 110 is not retained over rearward end 152 of sheath 144. The rearward end 153 of balloon 110 is accordingly not sealed to respective ends 151 and 152 of sheaths 132 and 144.

It is a particular feature of the embodiment of FIG. 2B that additional forward and rearward rigid collar elements 190 and 192 are mounted respectively on bending rubber sheath 144 and tubular sealing sheath 132 over selectably bendable reinforcement mesh 145 and reinforcement mesh 134 respectively, such as by crimp-mounting or by use of a suitable adhesive. Collar elements 190 and 192 are preferably formed of metal or a suitable plastic.

Rearward end 153 of inflatable balloon 110 is retained over rearward rigid collar element 192 preferably by a wire 156 wound thereabout. Rearward end 153 and wire 156 are sealed to rearward rigid collar element 192 and to tubular sealing sheath 132 by an adhesive 158, such as a medical grade epoxy M31-CL, commercially available from Henkel Corporation.

Forward end 176 of inflatable balloon 110 is retained over forward rigid collar element 190 preferably by a wire 178 wound thereabout. Forward end 176 and wire 178 are sealed to forward rigid collar element 190 and to Bending rubber sheath 144 by an adhesive 180, such as a medical grade epoxy M31-CL, commercially available from Henkel Corporation.

Thus it is appreciated that in contrast to the embodiment of FIG. 2A, forward end 176 of inflatable balloon 110 is not retained over forward end 174 of sheath 144 and is not sealed to rigid tip portion 170.

Filter 109 is preferably mounted onto an inner surface of sheath 144 underlying aperture 108 by any suitable technique, such as by the use of adhesive, for example a Polychloroprene based Contact Cement commercially available from Elmer's Products Inc. It is appreciated that a gas communication path extends between leak test port 114 via the interior volume 112, filter 109 and aperture 108 to balloon volume 116 at the interior of inflatable/deflatable balloon 110.

It is a particular feature of the embodiment of FIG. 2B that the length of balloon 110 is approximately similar to the separation of rigid elements 190 and 192 along the endoscope 100.

It is a further particular feature of a preferred embodiment of the present invention that rearward end 153 and forward end 176 of balloon 110 are mounted over rigid elements 190 and 192, such that the mounting of the balloon remains stable and useful over multiple uses thereof. This structure is both suitable for conventional reprocessing and provides a balloon-equipped endoscope which does not normally require balloon replacement.

Returning now to FIG. 1, it is seen that the endoscope 100 may be inserted, with balloon 110 in a deflated state, into a body passageway, such as a patient's large intestine. Stage A shows the endoscope 100 located in the transverse colon of the patient with balloon 110 in a deflated state and stage B shows the endoscope advanced through the patient's colon, to a location just rearwardly of the cecum with balloon 110 in a deflated state. Endoscopic inspection of the interior of the colon may take place during insertion of the endoscope.

It is a particular feature of the present invention that in stage C, while the endoscope is not yet moved from its position in stage B, the balloon 110 is inflated to an intermediate pressure state, preferably at a slidable frictional engagement pressure which is sufficient to provide frictional engagement between the outer surface of the balloon 110 and the inner surface of the colon engaged thereby but less than a pressure which anchors the balloon 110 thereat. Selectable inflation of balloon 110 to various pressures including an anchoring pressure and multiple selectable intermediate pressures is described in detail hereinbelow.

Thereafter, the operator pulls the endoscope 100 rearwardly, while the balloon 110 is at the aforesaid slidable frictional engagement pressure, thereby stretching the colon axially along its length and at least partially unfolding natural folds of the colon. In accordance with a preferred embodiment of the present invention, visual inspection of the colon takes place during the aforesaid retraction of the endoscope while the colon adjacent the forward end of the endoscope is axially stretched forwardly thereof. The aforesaid methodology of retracting the endoscope and thus stretching the colon and visually inspecting the interior of the colon while it is stretched is preferably carried out repeatedly along the colon from the cecum all of the way to the anus, such that the entire colon is systematically visually examined while each portion being examined is in a stretched state.

This inspection is shown generally in FIG. 1 at stage C when the forward end of endoscope 100 is located in the ascending (right) colon, thereafter at stage D when the forward end of endoscope 100 is located in the transverse colon and thereafter at stage E when the forward end of endoscope 100 is located in the descending (left) colon. It is a particular feature of the present invention that visual inspection of the colon while systematically axially stretching it to at least partially open the folds, enables detection of polyps and other potential and actual pathologies which might otherwise go undetected. For the purposes of the present patent application, visual inspection is inspection in which a clear line of sight is required or desirable, for example inspection in the IR or visible band, as distinguished from inspection in which a clear line of sight is not relevant, such as some types of X-ray inspection.

This particular feature of an embodiment of the present invention and the life-saving improvement over the prior art will be explained in greater detail hereinbelow with particular reference to FIGS. 3-6D below, which illustrate enhanced detection, during retraction of the endoscope, of polyps and other potential and actual pathologies which might otherwise go undetected, for example in the transverse colon, corresponding to stage D in FIG. 1.

It is a further particular feature of the present invention that balloon 110 is preferably configured for generally circumferentially uniform slidable frictional engagement with the interior wall of a body passageway, typically a tubular body portion, such as the colon, when inflated to a generally circumferentially uniform slidable frictional engagement pressure and displaced axially along said body passageway. This circumferentially uniform slidable frictional engagement is shown, for example in section C-C in FIG. 1.

It is also particular feature of the present invention that rearward axial displacement of balloon 110 in a body passageway under inspection when the balloon is in slidable frictional engagement with the interior wall of the body passageway, and preferably when being in generally circumferentially uniform slidable frictional engagement with the interior wall of the body passageway, provides at least partial removal of materials and fluids in the body passageway from the interior wall just prior to visual inspection thereof. Such materials and fluids may include, for example, food, feces, body fluids, blood and irrigation liquids injected by the endoscope 100 and could, if not removed, interfere with the visual inspection.

Preferably, the material and thickness of balloon 110 are selected and configured such that balloon 110 is radially compliant and conformable to the inner circumferential contour of the body passageway at the balloon engagement location, as to allow generally circumferentially uniform slidable frictional engagement of balloon 110 with the body passageway under inspection. An example of such a radially compliant and conformable balloon is a balloon having wall thickness of 20-30 microns, made of polyurethane type Tecothane D-1055D, commercially available from Lubrizol Corporation of 29400 Lakeland Boulevard Wickliffe, Ohio, USA.

The generally circumferentially uniform slidable frictional engagement pressure is preferably in the range of 3-40 millibar, more preferably in the range of 10-32 millibar and even more preferably in the range of 15-30 millibar.

Axial displacement of the endoscope balloon in generally circumferentially uniform slidable frictional engagement with the interior of the colon in order to achieve desired axial stretching of the colon is typically in the range of 10-100 millimeters, more likely in the range of 15-70 millimeters and sometimes in the range of 30-60 millimeters.

The axial stretching produced in the colon forwardly of CCD 101 of endoscope 100 in accordance with a preferred embodiment of the invention is preferably at least 25%, more preferably at least 35%, even more preferably at least 60% and still more preferably at least 100%.

Figure 3:
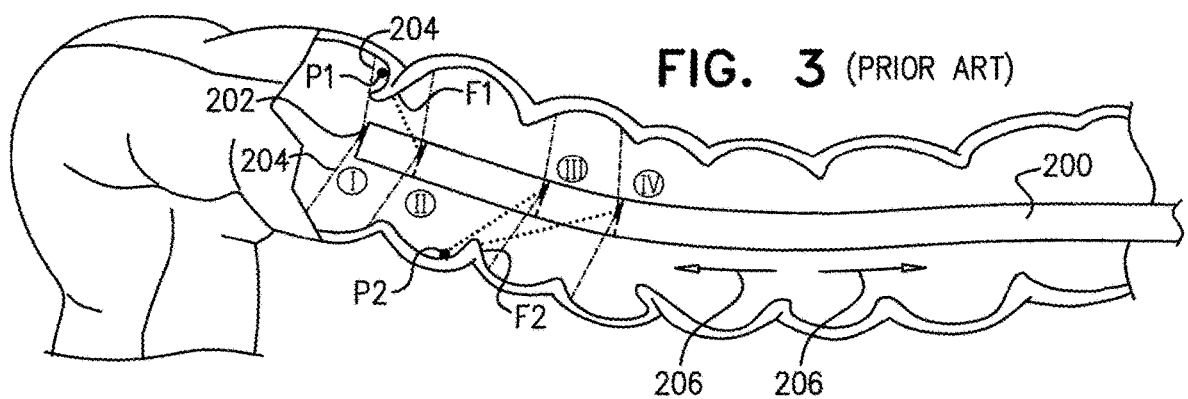
FIG. 3 is a simplified illustration of a prior art endoscopy technique showing multiple stages I, II, III & IV in overlay.

Reference is now made to FIG. 3, which is a simplified illustration of a prior art endoscopy technique in the transverse colon showing multiple stages I, II, III & IV in overlay, and to FIGS. 4A-4D, which are simplified illustrations of an image produced on a monitor in stages I, II, III & IV of the prior art endoscopy technique of FIG. 3. FIG. 3 and FIGS. 4A-4D show that polyps, here indicated by designations P1 and P2, which lie adjacent and forward of folds in the colon, may not be detected by prior art endoscopic techniques.

FIG. 3 shows a conventional endoscope 200 having a CCD 202 at its forward end. The field of view of CCD 202 is indicated by lines 204. The CCD 202 is shown at four different locations I, II, III & IV along the transverse colon, which are reached by either forward or rearward motion of the endoscope 200 axially along the colon, as indicated by arrows 206.

It is appreciated that irrespective of the direction of motion of the endoscope axially along the colon, polyp P1, which lies forward of a fold designated as F1 in the colon, is never seen by CCD 202 and is therefore not detected. This can be seen in FIGS. 4A & 4B, which are simplified illustrations of a simulated image produced on a monitor when the CCD 202 is at respective locations I & II, according to the prior art endoscopy technique shown in FIG. 3.

It is also appreciated that irrespective of the direction of motion of the endoscope axially along the colon, polyp P2, which lies forward of a fold designated as F2 in the colon, is not seen by CCD 202 when CCD 202 is at location IV and is seen by CCD 202, when CCD 202 is at location III. This can be seen in FIGS. 4D & 4C respectively, which are simplified illustrations of a simulated image produced on a monitor when the CCD 202 is at respective locations IV & III, according to the prior art endoscopy technique shown in FIG. 3. The limited viewability of polyp P2 increases the chances that it may be missed during a routine colonoscopy.

In the prior art exemplified in FIGS. 3 & 4A-4D, as distinguished from the present invention, systematic axial stretching of the colon adjacent to and forward of the CCD is not provided.

Reference is now made to FIGS. 5A, 5B, 5C & 5D, which are simplified illustrations of endoscopy methodology in accordance with an embodiment of the present invention at CCD locations I, II, III & IV, corresponding to CCD locations I, II, III & IV in prior art FIG. 3. Reference is also made to FIGS. 6A, 6B, 6C & 6D, which are simplified illustrations of a simulated image produced on monitor 104, forming part of the system of FIG. 1, at CCD locations I, II, III & IV of corresponding FIGS. 5A-5D in accordance with an embodiment of the present invention.

It is seen from a comparison of FIGS. 5A-5D & 6A-6D of an embodiment of the present invention and FIG. 3 & FIGS. 4A-4D of the prior art, that in an embodiment of the present invention the colon adjacent to and forward of CCD 101 is axially stretched, thus reducing or eliminating the protrusion of folds, such as folds F1 and F2, thereby enabling polyps and other potential and actual pathologies, such as polyps P1 and P2, which were fully or partially hidden from view by respective folds F1 and F2 when the colon was in a generally non-axially stretched state, as shown in FIG. 3, to be seen by CCD 101 and thus be detected.

Figure 4A:
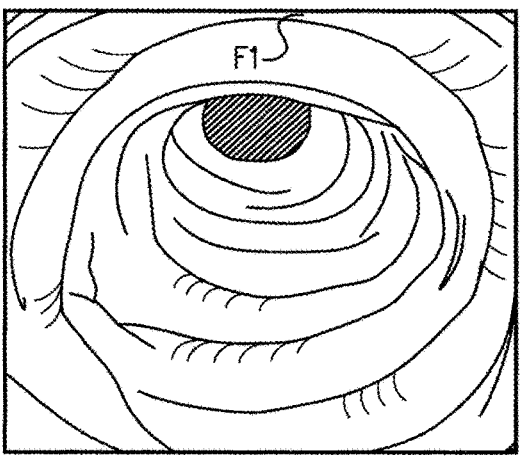
FIGS. 4A, 4B, 4C and 4D are simplified illustrations of an image produced on a monitor in stages I, II, III & IV of the prior art endoscopy technique of FIG. 3.
Figure 4B:
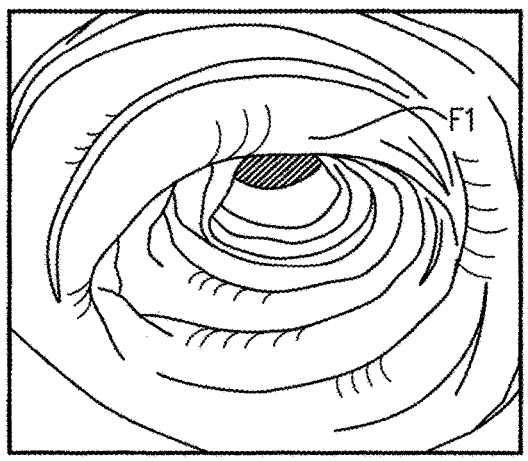
Figure 4C:
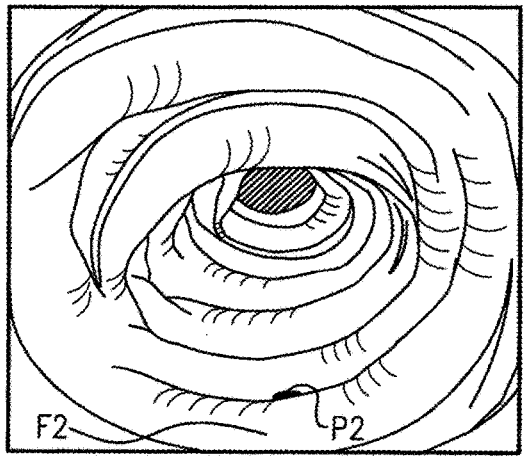
Figure 4D:
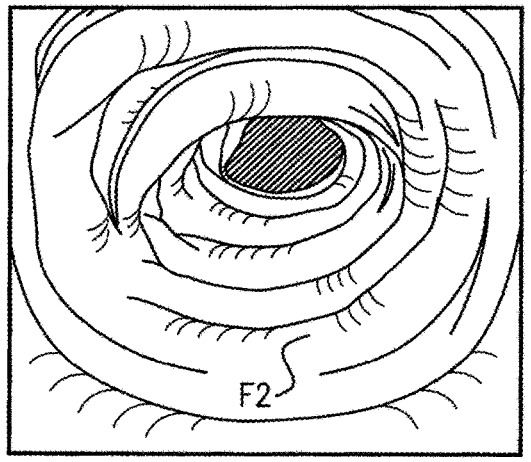
Figure 5A:
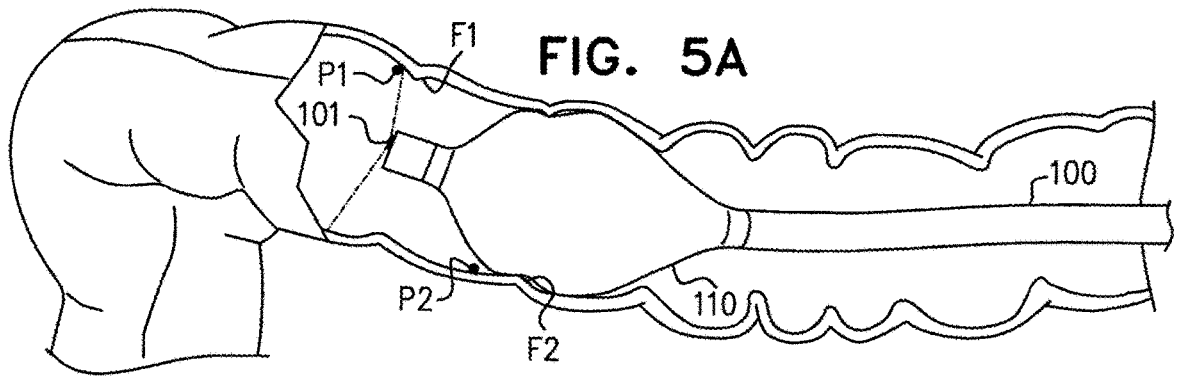
FIGS. 5A, 5B, 5C and 5D are simplified illustrations of multiple stages of endoscopy methodology, corresponding to stages I, II, III & IV in FIG. 3 in accordance with a preferred embodiment of the present invention.
Figure 5B:
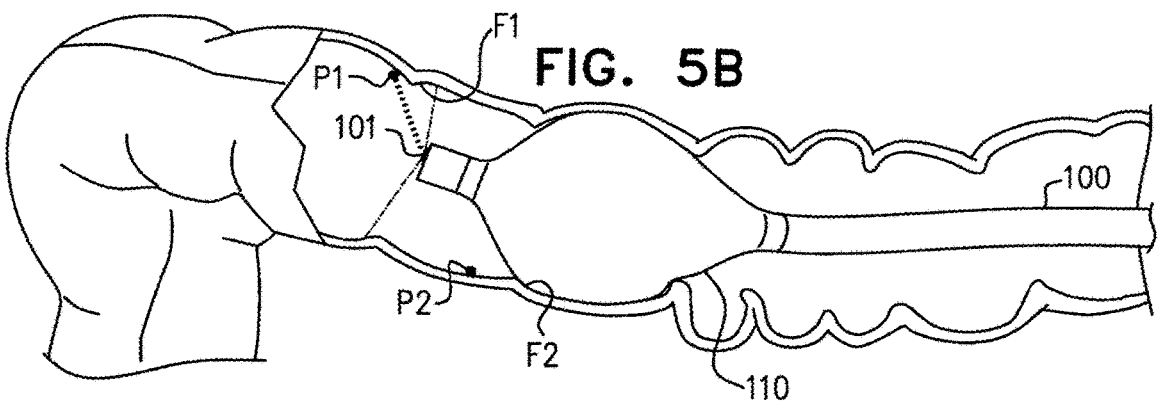
Figure 5C:
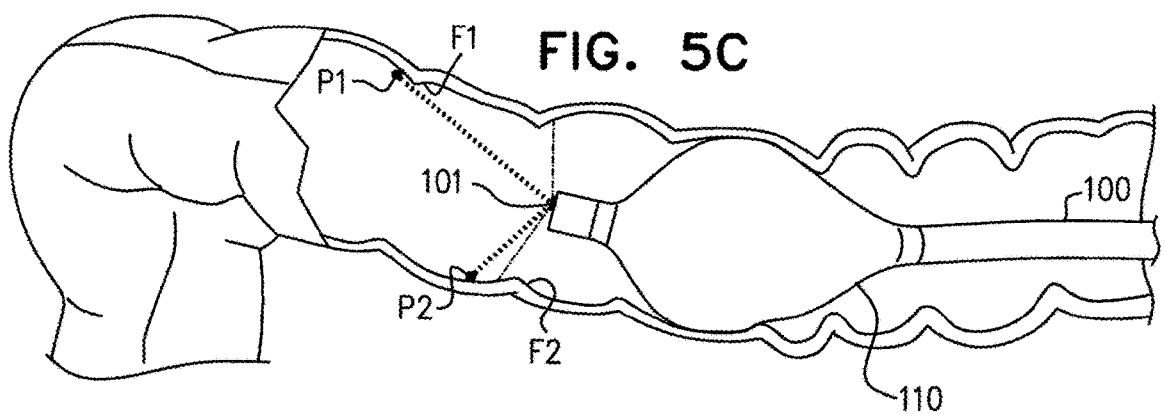
Figure 5D:
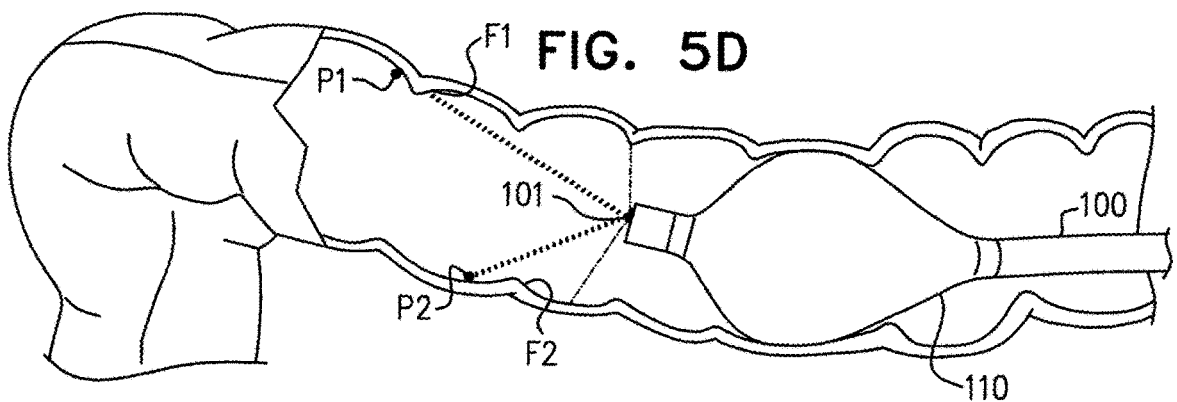
Figure 6A:
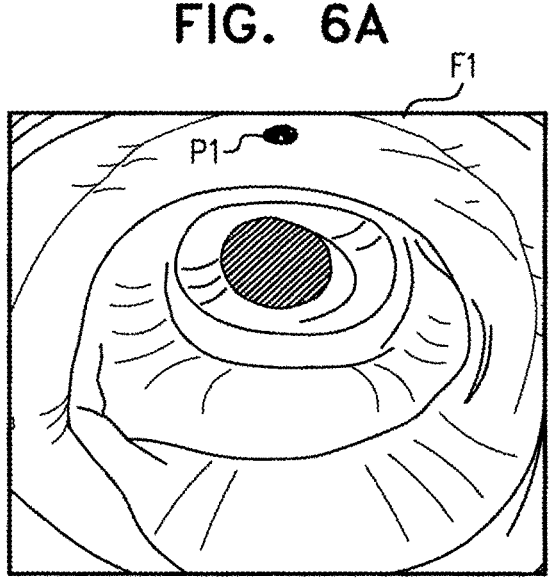
FIGS. 6A, 6B, 6C and 6D are simplified illustrations of an image produced on a monitor forming part of the system of FIG. 1, at the stages I, II, III & IV of corresponding FIGS. 5A-5D.
Figure 6B:
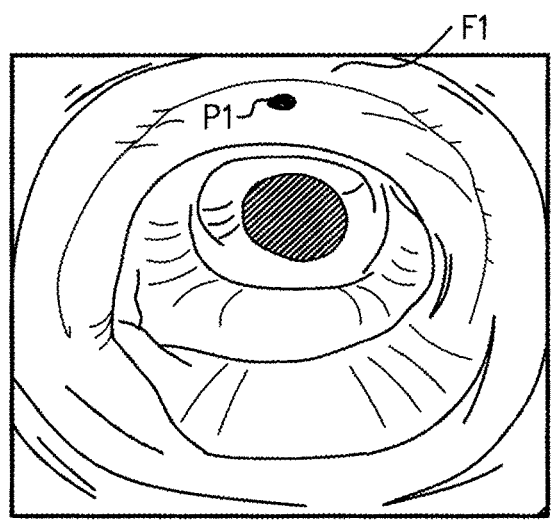
Figure 6C:
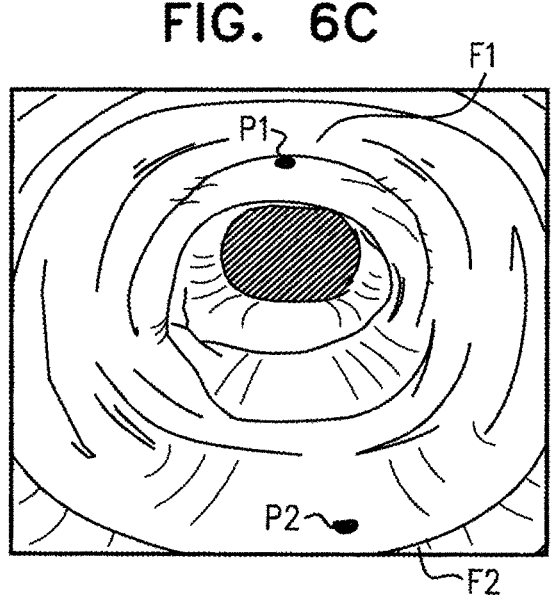
Figure 6D:
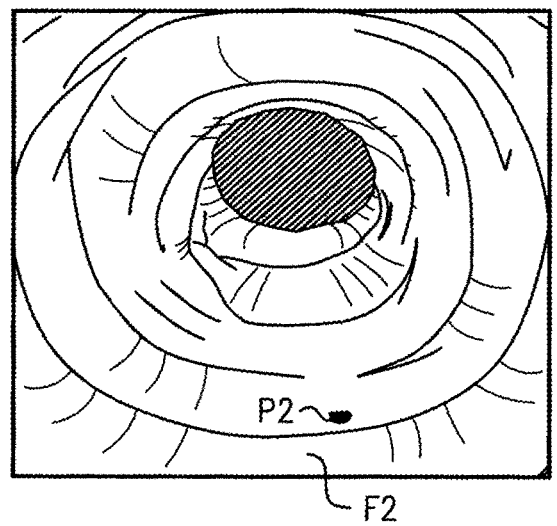

Specifically, FIGS. 5A & 5B and 6A & 6B show detection of polyp P1 when the CCD 101 is at locations I & II, whereas, in contrast, as seen in FIG. 3 and FIGS. 4A and 4B, polyp P1 was hidden by fold F1 in the colon. FIGS. 5C & 5D show detection of polyp P2 when the CCD 102 is at locations III and IV, whereas, in contrast, as seen in FIG. 3 and FIG. 4D, polyp P2 was hidden by fold F2 in the colon when the CCD 202 was at location IV. FIGS. 3 and 4C show detection of polyp P2 when the CCD 202 was at location III. With respect to polyp P2, it is appreciated that the present invention provides a significant extension of the range of CCD locations over which it can be viewed and thus a significant increase in the chances that it will be detected.

Another important feature of the present invention will now be described with reference to FIG. 7, which is a simplified illustration of the transverse colon in unstretched and stretched states and to FIG. 8, which is a simplified illustration of images produced on a monitor forming part of the system of FIG. 1 when viewing the transverse colon in the unstretched and stretched states of FIG. 7.

By considering FIGS. 7 and 8 together it is seen that stretching of the colon is not only important for providing lines of sight to polyps and other potential and actual pathologies which might be otherwise blocked by folds in the colon, as described just above. FIGS. 7 and 8 illustrate that some polyps and other potential and actual pathologies are made more visible by stretching the colon. This stretching causes such polyps and other potential and actual pathologies to protrude inwardly of the colon to an extent which is enhanced. Furthermore, stretching of the colon creates a smoother and more visually uniform background against which such polyps and other potential and actual pathologies can more readily be seen by an operator and thus creates enhanced visual contrast between polyps and other potential and actual pathologies and the interior of the colon.

FIGS. 7 and 8 both show a shallow polyp, designated as SP, which is hardly visible when the colon is in an unstretched state and is much more visible when the colon is in a stretched state.

Figure 9A:
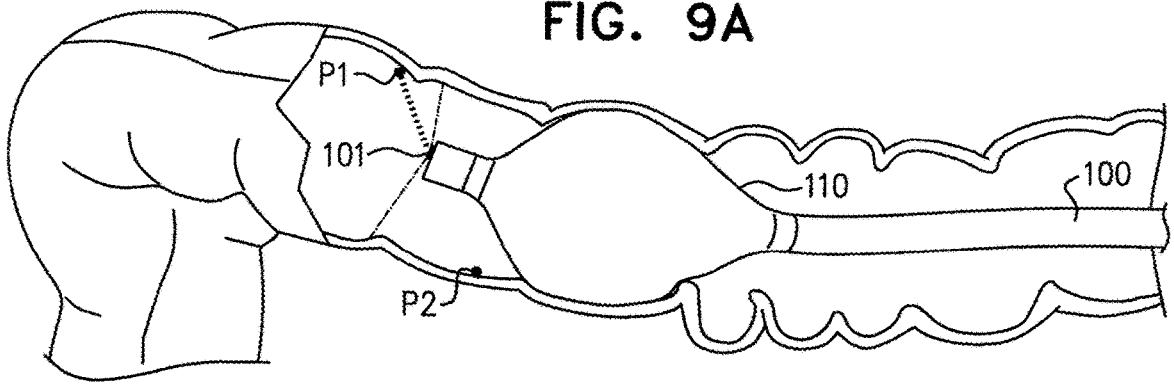
FIGS. 9A, 9B and 9C are simplified illustrations of further multiple stages of endoscopy methodology in which balloon anchoring is provided in accordance with a preferred embodiment of the present invention.
Figure 9B:
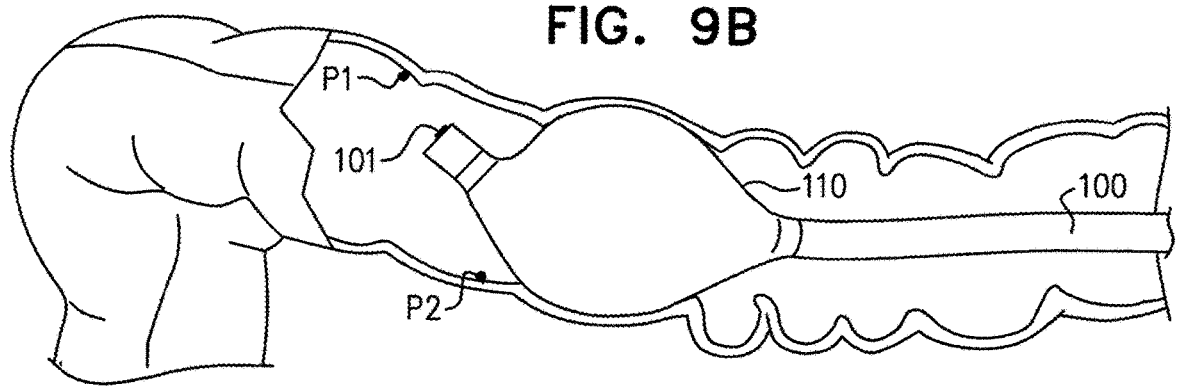
Figure 9C:
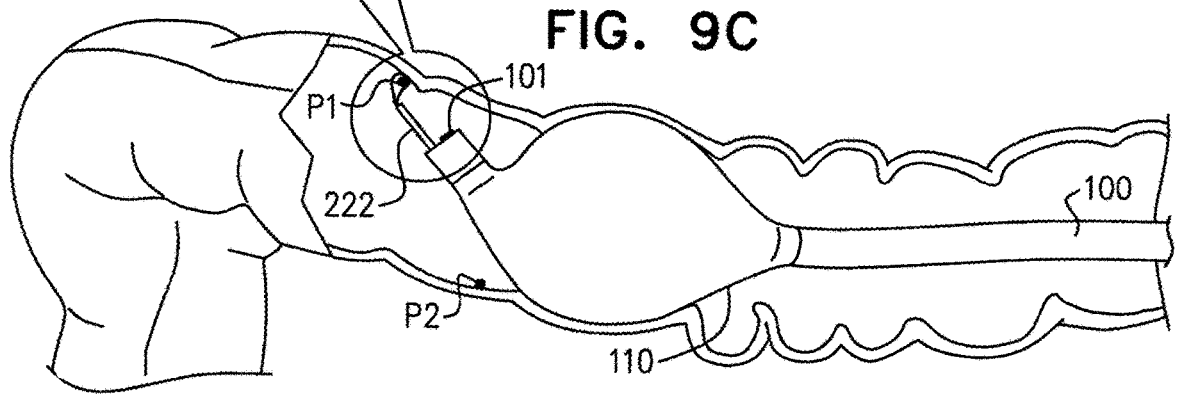

Reference is now made to FIGS. 9A, 9B and 9C, which are simplified illustrations of further multiple stages of endoscopy methodology in which balloon anchoring is provided in accordance with a preferred embodiment of the present invention. FIG. 9A corresponds to FIG. 5B and shows detection of polyp P1. FIG. 9B shows that upon detection of polyp P1, balloon 110 (FIGS. 1, 2A, 2B & 5A-5D) may be inflated to an anchoring pressure, such as a pressure between 50-80 millibars, well beyond the intermediate inflation pressure employed in the methodology of FIGS. 5A-5D, thus anchoring the balloon 110 in the colon. FIG. 9C shows removal of polyp P1 using a conventional endoscope tool 222.

It is a particular feature of an embodiment of the present invention that the balloon 110 can be inflated to an anchoring pressure as well as to a slidable frictional engagement pressure.

Selection between anchoring pressure and slidable frictional engagement pressure is preferably effected by the operator through the user interface of inflation/deflation system 130. Preferably, switching between an anchoring state and a slidable frictional engagement pressure state of balloon 110 may be performed by the operator as needed during the endoscopy procedure.

It is another particular feature of an embodiment of the present invention that the ratio between the anchoring pressure and the intermediate slidable frictional engagement pressure is in the range of 1.3-7, and preferably in the range of 2-4.5. In accordance with an embodiment of the present invention, the anchoring pressure is at least 60 millibars and the intermediate slidable frictional engagement pressure is not higher than 35 millibars.

It is a particular feature of the present invention that the operator may select between at least one anchoring pressure state and multiple alternative intermediate slidable frictional engagement pressure states, typically two to four different intermediate pressure states. In a preferred embodiment of the invention, three different selectable intermediate pressure states are provided by system 130 (FIG. 1), such as in the ranges of 3-15 millibars, 15-23 millibars and 23-35 millibars. Alternatively three different intermediate pressure state ranges of 10-18, 18-25 and 25-35 millibars may be provided. As a further alternative, the ranges may be 13-18, 22-25 and 28-32 millibars. Preferably, the anchoring pressure may be in the range of 50-85 millibars. More preferably, the anchoring pressure may be in the range of 60-80 millibars. Still more preferably, the anchoring pressure may be in the range of 65-80 millibars. Most preferably, the anchoring pressure may be in the range of 65-75 millibars.

In a colonoscopy procedure conducted on Dec. 21, 2011 in a gastroenterology clinic by a physician on the staff of the Tel-Aviv Medical Center, Tel-Aviv, Israel, the system and methodology generally described hereinabove with reference to FIGS. 1-9C & 12-14 was employed.

In this colonoscopy procedure, and upon employing the methodology described hereinabove, colon stretching forwardly of the endoscope in the approximate range of 30%-60% was produced. An intermediate slidable frictional engagement pressure in the range of 10-18 millibars was employed. Protrusion of colon folds inwardly to the colon interior volume decreased from typically 6-20 millimeters to 3-10 millimeters.

When intermediate slidable frictional engagement pressure in the range of 25-32 millibars was employed, colon stretching forwardly of the endoscope in the approximate range of 50%-100% was produced. A corresponding decrease of protrusion of colon folds inwardly to 0-7 millimeters was achieved. In this colonoscopy procedure, two polyps were detected by the endoscope while inspecting the colon during insertion with the balloon deflated. Three additional polyps, not detected during insertion, one of which was a shallow polyp, were detected by the endoscope during retraction thereof with the balloon inflated to a slidable frictional engagement pressure and thus with the colon being stretched forwardly of the endoscope, thereby reducing inward protrusion of folds and enhancing visual contrast, as described hereinabove with reference to FIGS. 1-9C & 12-14. Prior to polyp removal with a conventional endoscope tool, anchoring pressure in the range of 65-75 millibars was employed in this procedure to anchor the balloon to the colon rearwardly of the polyp to be removed, thereby stabilizing the endoscope during polyp removal.

It was observed in this procedure that in the descending (left) colon, intermediate slidable frictional engagement pressure in the range of 18-26 millibars was sufficient to produce colon stretching forwardly of the endoscope. A similar extent of colon stretching was produced in the ascending (right) colon by a higher intermediate pressure in the range of 25-32 millibars.

It is thus appreciated that different locations in a tubular body portion under examination may require different intermediate pressures, and that selectability between several different intermediate pressures or intermediate pressure ranges, either manually by the operator or automatically by the inflation/deflation system, is beneficial and enables the operator or the system to match the intermediate pressure to the extent of folding and to the required amount of stretching.

It is a particular feature of the present invention that a life-saving improvement over the prior art is realized in that polyps that were not detected in the conventional inspection method were detected.

In addition, the procedure described hereinabove demonstrated that different intermediate pressures are suitable for different portions of the colon, and specifically that the ascending (right) colon requires typically a higher intermediate pressure than the ascending (left) colon.

It was observed in this procedure that retraction of the endoscope with the balloon engaging the colon in slidable frictional engagement therewith provided cleaning of the colon forwardly of the endoscope and removal of materials and fluids in the colon from the interior wall of the colon prior to visual inspection thereof.

In a second colonoscopy examination performed on Dec. 21, 2011 generally employing the system and methodology of FIGS. 1-9C & 12-14, no polyps were detected either during advancement with the balloon deflated or during withdrawal.

In a third colonoscopy procedure conducted on Dec. 29, 2011 generally employing the system and methodology of FIGS. 1-9C & 12-14, in the same clinic as the first and second colonoscopy procedures described hereinabove, no polyps were detected while inspecting the colon during insertion and two polyps were detected during retraction of the endoscope with the balloon inflated to a slidable frictional engagement pressure and thereby stretching the colon forwardly of the endo scope, reducing folds and enhancing visual contrast.

In a fourth colonoscopy procedure, performed on Dec. 29, 2011 generally employing the system and methodology of FIGS. 1-9C & 12-14, no polyps were detected. In a fifth colonoscopy procedure, performed on Dec. 29, 2011 generally employing the system and methodology of FIGS. 1-9C & 12-14, no polyps were detected during insertion and two polyps were detected during retraction of the endoscope with the balloon inflated to an intermediate slidable frictional engagement pressure and thereby stretching the colon forwardly of the endoscope, reducing folds and enhancing visual contrast.

The aforesaid early clinical experience with the system and methodology of the embodiment of FIGS. 1-9C & 12-14 of the present invention demonstrated the life-saving improvement over the prior art in the enhanced detection provided by of the system and methodology of the present invention as described hereinabove with reference to FIGS. 1-9C & 12-14. Polyps that were not detected in the conventional inspection method were detected by the aforementioned invention.

Figure 11:
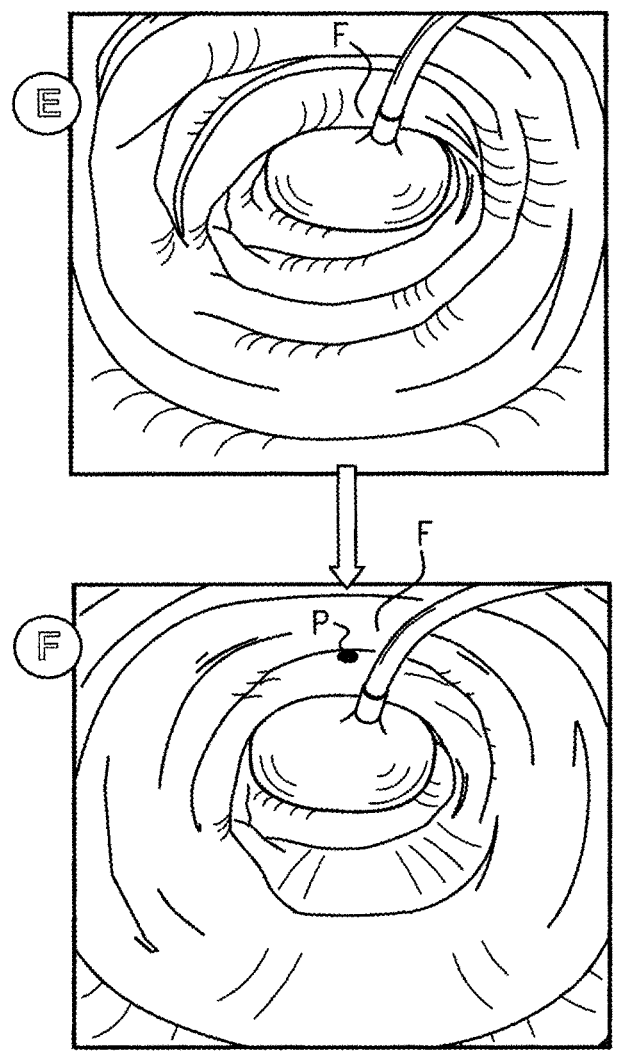
FIG. 11 is a simplified illustration of images produced on a monitor forming part of the system of FIG. 10 at respective stages E & F shown in FIG. 10.

Reference is now made to FIG. 10, which is a simplified illustration of an endoscope system and methodology constructed and operative in accordance with another preferred embodiment of the present invention and to FIG. 11, which is a simplified illustration of images produced on a monitor forming part of the system of FIG. 10 at respective stages E & F shown in FIG. 10.

FIG. 10 illustrates the general structure and operation of another embodiment of an endoscope system and methodology, constructed and operative in accordance with the present invention. As seen in FIG. 10, an endoscope 300, having a CCD 301 at a forward end thereof, is connected to an endoscope system 302 including a monitor 304. Alternatively CCD 301 may be replaced by any other suitable detector.

The endoscope 300 may be a conventional endoscope, such as an EC-3470LK video colonoscope or a VSB-3430K video enteroscope, the endoscope system 302 may be a conventional endoscope system, such as a console including a EPK-1000 video processor, and the monitor 304 may be a conventional monitor, such as a SONY LMD-2140MD medical grade flat panel LCD monitor, all commercially available from Pentax Europe GmbH, 104 Julius-Vosseler St., 22527 Hamburg, Germany.

The endoscope may be an endoscope as described in Published PCT Application No. WO 2011/111040, published on Sep. 15, 2011, the disclosure of which is hereby incorporated by reference, or an endoscope as described hereinabove with reference to FIGS. 1-9C.

In accordance with a preferred embodiment of the present invention, a balloon-equipped endoscope tool 310 is provided. The balloon-equipped endoscope tool 310 may be identical to that described in Published PCT Applications No. WO2008/142685, published on Nov. 27, 2008, and WO2010/137025, published on Dec. 2, 2010, the disclosures of which are hereby incorporated by reference. The endoscope tool 310 preferably comprises an endoscope tool inflation tube 312 which is coupled to an endoscope tool balloon 314 for selectable inflation/deflation thereof.

It is seen that the endoscope 300 may be inserted into a body passageway, such as a patient's large intestine. Stage A shows the endoscope 300 located in the ascending (right) colon of the patient, rearwardly of the cecum. Stage B shows the endoscope tool 310 having been inserted through a port 320 of an instrument channel 322 of endoscope 300 and positioned forwardly of CCD 301. The balloon 314 is shown inflated to an anchoring state at a location inside the patient's colon which is adjacent to and rearwardly spaced from the cecum.

At stage C, the endoscope tool 310 is shown having been pushed forwardly with respect to its position at stage B and preferably also with respect to the CCD 301. This is preferably achieved by pushing the inflation tube 312 forwardly through the instrument channel 322 by an operator who grasps the inflation tube 312 just rearwardly of the port 320 and pushes the inflation tube 312 forwardly, and preferably also by the operator who gently and slightly retracts the endoscope 300. The forward pushing of the anchored balloon 314 alone or in combination with retraction of the endoscope 300 produces desired axial stretching of the colon, as seen by comparing the illustrated Stage B with the illustrated Stage C. Endoscopic inspection of the interior of the colon preferably takes place when the colon is stretched. As noted above with reference to FIGS. 1-9C, stretching the colon axially along its length at least partially unfolds natural folds of the colon. In accordance with a preferred embodiment of the present invention, visual inspection of the colon takes place while the colon adjacent the forward end of the endoscope is axially stretched forwardly thereof.

The aforesaid methodology of stretching the colon and visually inspecting the interior of the colon while it is stretched is preferably carried out repeatedly along the colon from the cecum all of the way to the anus, such that the entire colon is systematically visually examined while each portion being examined is in a stretched state. In this embodiment the following steps are preferably repeated multiple times systematically along the entire length of the colon: positioning the endoscope tool balloon 314 forwardly of the CCD 301;

inflating and thus anchoring the endoscope tool balloon 314 in the colon;

thereafter pushing the endoscope tool balloon 314 forwardly, thereby stretching the colon to enable enhanced viewing of the interior of the colon with reduced folds; and visually inspecting the stretched portion of the colon It is appreciated that the foregoing methodology is applicable not only to the colon but also to other tubular body portions, such as the small intestine, the esophagus and other body passageways.

This inspection is shown generally in FIG. 10 at stage C when the forward end of endoscope 300 is located in the ascending (right) colon, and thereafter at stages D, E and F when the forward end of endoscope 300 is located in the transverse colon. At stage D, retraction of the endoscope tool 310 relative to the endoscope 300, with balloon 314 in a generally deflated state, is shown. At stage E, balloon 314 is seen to be inflated and anchored in the colon and at stage F, the balloon 314 is seen to have been pushed forward, thus stretching the colon forwardly of CCD 301.

As noted above, it is a particular feature of the present invention that visual inspection of the colon while systematically axially stretching it to at least partially open the folds, enables detection of polyps and other potential and actual pathologies which might otherwise go undetected. For the purposes of the present patent application, visual inspection is inspection in which a clear line of sight is required or desirable, for example inspection in the IR or visible band, as distinguished from inspection in which a clear line. of sight is not relevant, such as some types of X-ray inspection.

This particular feature of an embodiment of the present invention and the life-saving improvement over the prior art will be explained in greater detail hereinbelow with particular reference to FIG. 11, which illustrates enhanced detection, during stretching of the colon, of polyps and other potential and actual pathologies which might otherwise go undetected.

It is seen that at Stage E in FIG. 10 the balloon 314 is inflated to an anchoring state but the colon is not yet stretched. Monitor 304 shows an image of a portion of the colon forward of CCD 301. FIG. 11 shows at E, a simulated image of what is seen on monitor 304 at Stage E in FIG. 10, prior to stretching the colon. FIG. 11 shows at F a simulated image of generally the same portion of the colon that is seen on monitor 304 at stage F in FIG. 10, when the colon is stretched. A polyp P, hidden from view by a fold F of the colon at stage E, is now seen and can be treated.

It is a particular feature of a preferred embodiment of a balloon-equipped endoscope tool of the present invention that some polyps and other potential and actual pathologies are made more visible by stretching the colon, as described hereinabove with reference to FIGS. 10 & 11. This stretching causes such polyps and other potential and actual pathologies to protrude inwardly of the colon to an extent which is enhanced. Furthermore, stretching of the colon creates a smoother and more visually uniform background against which such polyps and other potential and actual pathologies can more readily be seen by an operator and thus creates enhanced visual contrast between polyps and other potential and actual pathologies and the interior of the colon.

Figure 12:
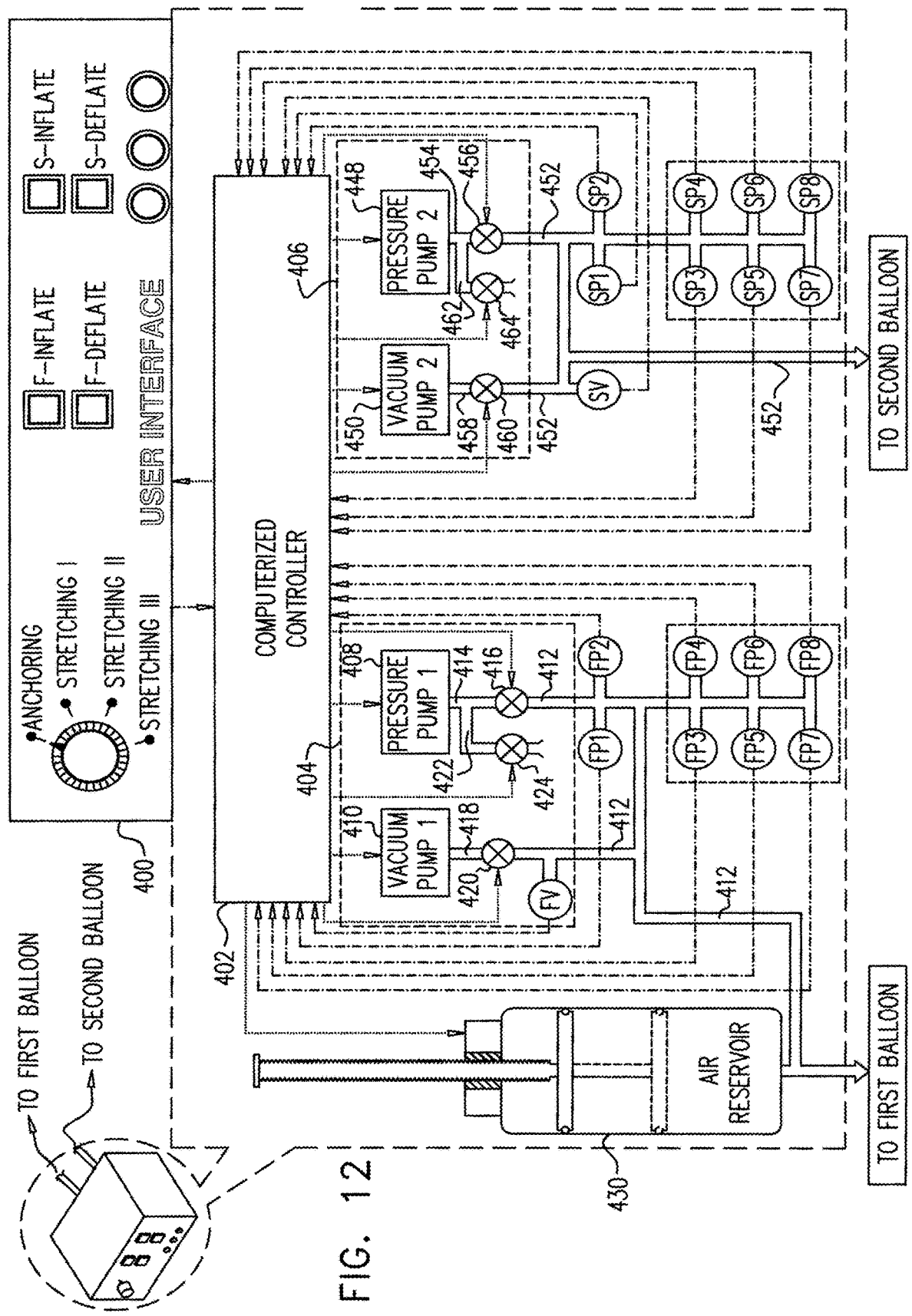
FIG. 12 is a simplified block diagram of a balloon inflation/deflation system employed in either of the embodiments shown in FIGS. 1 and 10.
Figure 13A:
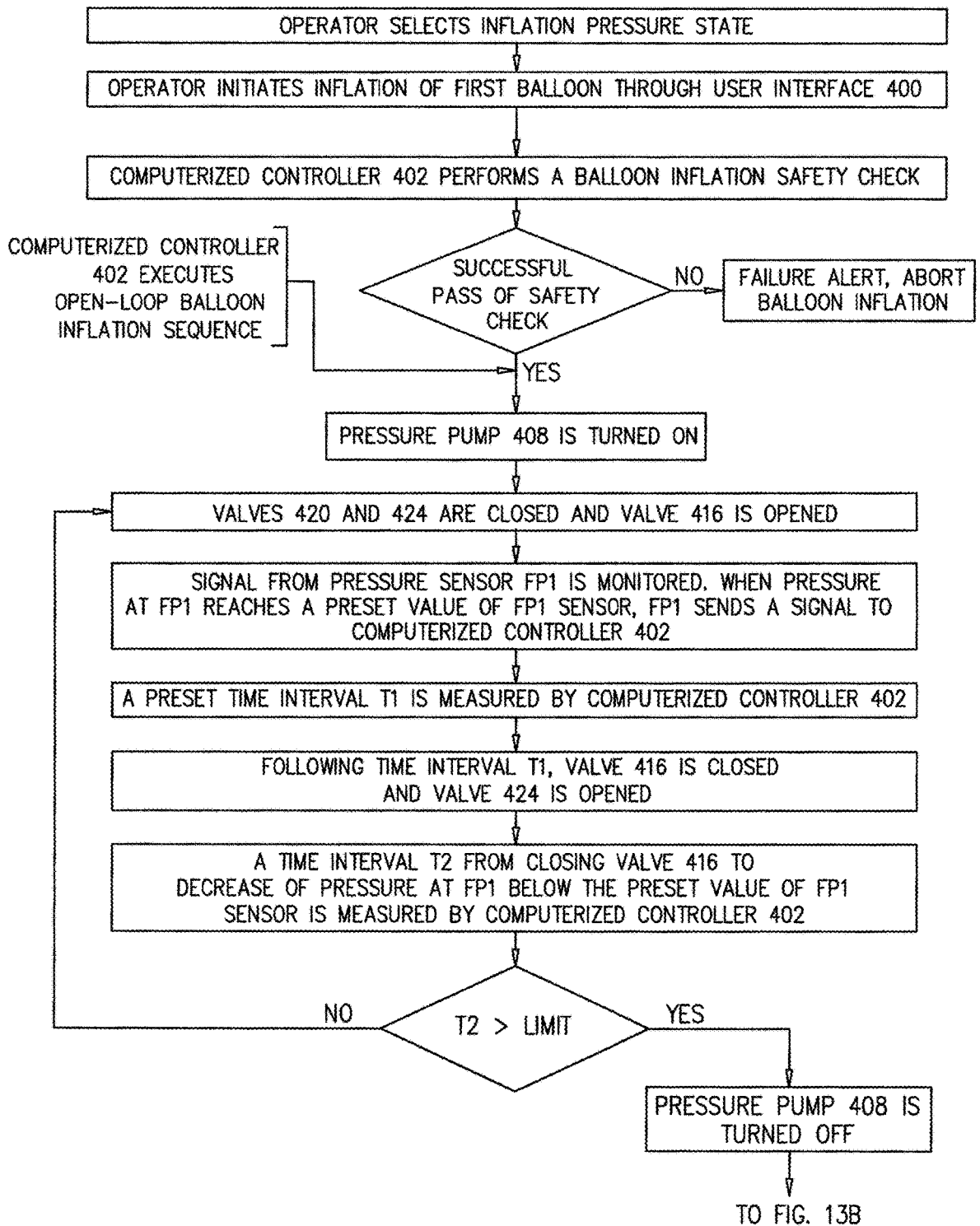
FIGS. 13A & 13B are together a simplified flow chart illustrating a preferred mode of operation of the balloon inflation/deflation system of FIG. 12.
Figure 13B:
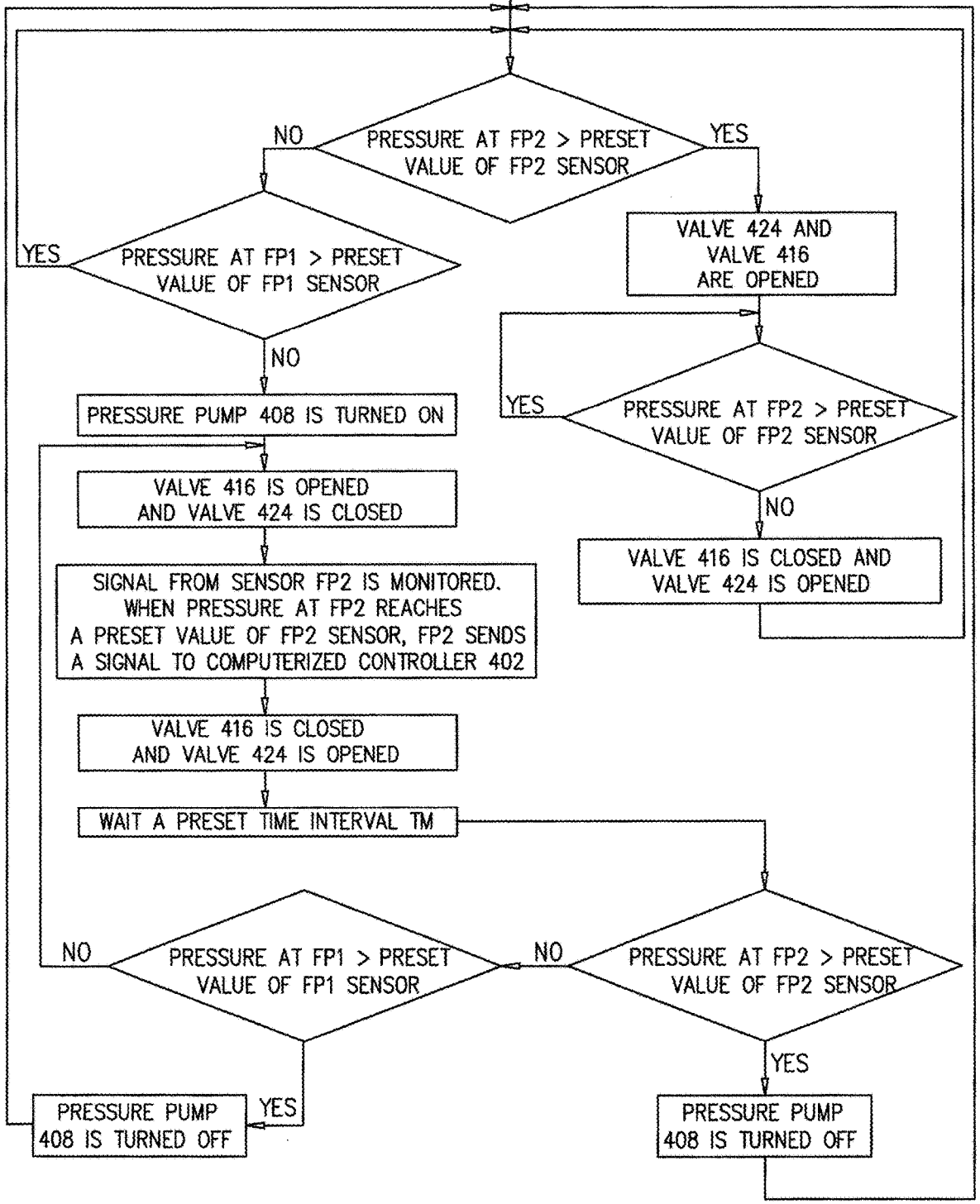

Reference is now made to FIG. 12, which is a simplified block diagram of a balloon inflation/deflation system which is a preferred embodiment of the balloon inflation/deflation system 130 employed in either of the embodiments shown in FIGS. 1 and 10 and to FIGS. 13A & 13B, which are together a simplified flow chart illustrating a preferred mode of operation of the balloon inflation/deflation system of FIG. 12.

It is a particular feature of an embodiment of the present invention that the balloon inflation/deflation system is capable of carrying out a balloon inflation/deflation operation in substantially less time than in prior art devices, preferably performing balloon inflation at least 2-3 times faster than prior art devices. This may be extremely significant in terms of overall treatment time, since up to approximately 20 balloon inflations may be carried out in a balloon endoscopy procedure.

Turning initially to FIG. 12, it is seen that there is provided a balloon inflation/deflation system including a user interface 400, typically comprising one or more buttons, switches or pedals and one or more visually sensible status indication lights, dials or displays. The user interface 400 communicates with a computerized controller 402, such as a suitably programmed microcontroller, important parts of the functionality thereof being described in detail in FIGS. 13A & 13B.

Computerized controller 402 preferably controls the operation of first and second inflation/deflation pump assemblies 404 and 406 which are respectively configured for use with an endoscope balloon, such as balloon 110 (FIG. 1) and with an endoscope tool balloon, such as balloon 314 (FIG. 10). It is appreciated that pump assemblies 404 and 406 may each be used with a different endoscope balloon or endoscope tool balloon. It is appreciated that alternatively separate computerized controllers 402 may be provided for each of the first and second inflation/deflation pump assemblies 404 and 406 or that either of the first and second inflation/deflation pump assemblies 404 and 406 may be obviated. It is further appreciated that only a single inflation/deflation pump assembly may be provided for selectable use with either or both of an endoscope balloon and an endoscope tool balloon. It is additionally appreciated that multiple inflation/deflation pump assemblies may be provided for use with multiple endoscope balloons.

First inflation/deflation pump assembly 404 preferably comprises a pressure pump 408 and a vacuum pump 410, each of which is coupled to the interior of a balloon via a branched inflation/deflation channel 412 and an inflation/deflation tube, such as inflation/deflation tube 131 (FIG. 1). Branched inflation/deflation channel 412 includes a pressure pump connection branch 414 controlled by a valve 416 and a vacuum pump connection branch 418 controlled by a valve 420. An exhaust channel 422 is coupled to pressure pump connection branch 414 between valve 416 and pressure pump 408 and is controlled by a valve 424.

Disposed in pressure communication with inflation/deflation channel 412 as it extends from first inflation/deflation pump assembly 404 to the interior of an endoscope balloon, such as balloon 110 (FIG. 1) is an array of pressure level indicators, here designated FP1-FP8, which are preferably binary pressure indicators, each providing an indication to computerized controller 402 whether the pressure in inflation/deflation channel 412 thereat is above a predetermined pressure threshold. In the preferred embodiment described hereinbelow in greater detail with reference to FIGS. 13A & 13B, typical pressure thresholds of pressure level indicators FP1-FP8 are as follows:

| Pressure level indicator | Threshold pressure |
| --- | --- |
| FP1 | 60 millibar |
| FP2 | 75 millibar |
| FP3 | 10 millibar |
| FP4 | 15 millibar |
| FP5 | 18 millibar |
| FP6 | 23 millibar |
| FP7 | 26 millibar |
| FP8 | 32 millibar |

It is appreciated that any alternative suitable threshold values of pressure indicators FP1-FP8 may be employed. Preferably, the FP1 threshold may be in the range of 55-67 millibar and the FP2 threshold, which must be higher than the FP1 threshold, may be in the range of 63-80 millibar. The FP3 threshold may be in the range of 4-18 millibar and the FP4 threshold, which must be higher than the FP3 threshold, may be in the range of 13-23 millibar.

The FP5 threshold may be in the range of 13-25 millibar and the FP6 threshold, which must be higher than the FP5 threshold, may be in the range of 17-30 millibar. The FP7 threshold may be in the range of 20-30 millibar and the FP8 threshold, which must be higher than the FP7 threshold, may be in the range of 24-40 millibar. Alternatively, the thresholds of FP3, FP5 and FP7 may be identical and may be in the range of 7-20 millibar.

Disposed in pressure communication with inflation/deflation channel 412 as it extends from first inflation/deflation pump assembly 404 to the interior of an endoscope balloon, such as balloon 110 (FIG. 1) is a vacuum level indicator FV, which is preferably a binary vacuum indicator, providing an indication to computerized controller 402 whether the vacuum in inflation/deflation channel 412 thereat is above a predetermined pressure threshold.

It is appreciated that one or more of pressure level indicators FP1-FP8 and vacuum level indicator FV may be replaced by at least one differential continuous pressure/vacuum sensor, such as a Board Mount Pressure/Vacuum sensor, Part Number NSC-DIP-DR-150PD-UNV, commercially available from Honeywell International Inc. of 101 Columbia Road, Morristown, N.J. 07962, USA.

In accordance with a preferred embodiment of the present invention, an air reservoir 430 is provided in pressure communication with inflation/deflation channel 412. Preferably the volume of reservoir 430 is selectable by the operator via operation of the user interface 400 and the computerized controller 402. Preferably, the volume of air reservoir 430 may be selectably variable in the range of 0-900 cc. The volume of air reservoir 430 may be selected by the operator, for example, according to the specific endoscope model being used. It is appreciated that a relatively larger volume of air reservoir 430 may be selected for certain models of endoscopes which have a relatively small interior volume 112, such that the ratio between the sum of interior volume 112 and air reservoir 430, and the inflated balloon volume 116, will be maintained within an acceptable range, examples of which are set forth hereinabove. Correspondingly, a relatively smaller volume of air reservoir 430 may be selected for certain models of endoscopes which have a relatively larger interior volume 112, such that the ratio between the sum of interior volume 112 and air reservoir 430, and the inflated balloon volume 116, will be maintained within the aforementioned acceptable range.

Second inflation/deflation pump assembly 406 preferably comprises a pressure pump 448 and a vacuum pump 450, each of which is coupled to the interior of a balloon via a branched inflation/deflation channel 452 and an inflation/deflation tube, such as tool balloon inflation tube 312 (FIG. 10). Branched inflation/deflation channel 452 includes a pressure pump connection branch 454 controlled by a valve 456 and a vacuum pump connection branch 458 controlled by a valve 460. An exhaust channel 462 is coupled to pressure pump connection branch 454 between valve 456 and pressure pump 448 and is controlled by a valve 464.

Disposed in pressure communication with inflation/deflation channel 452 as it extends from second inflation/deflation pump assembly 406 to the interior of an endoscope tool balloon, such as balloon 314 (FIG. 10), is an array of pressure level indicators, here designated SP1-SP8, which are preferably binary pressure indicators, each providing an indication to computerized controller 402 whether the pressure in inflation/deflation channel thereat is above a predetermined pressure threshold. In the preferred embodiment described hereinbelow in greater detail with reference to FIGS. 13A & 13B, typical pressure thresholds of pressure level indicators SP1-SP2 are as follows:

| Pressure level indicator | Threshold pressure |
| --- | --- |
| SP1 | 60 millibar |
| SP2 | 75 millibar |
| SP3 | 10 millibar |
| SP4 | 15 millibar |
| SP5 | 18 millibar |

| Pressure level indicator | Threshold pressure |
| --- | --- |
| SP6 | 23 millibar |
| SP7 | 26 millibar |
| SP8 | 32 millibar |

It is appreciated that any alternative suitable threshold values of pressure indicators SP1-SP8 may be employed. Preferably, the SP1 threshold may be in the range of 55-67 millibar and the SP2 threshold, which must be higher than the SP1 threshold, may be in the range of 63-80 millibar. The SP3 threshold may be in the range of 4-18 millibar and the SP4 threshold, which must be higher than the SP3 threshold, may be in the range of 13-23 millibar.

The SP5 threshold may be in the range of 13-25 millibar and the SP6 threshold, which must be higher than the SPS threshold, may be in the range of 17-30 millibar. The SP7 threshold may be in the range of 20-30 millibar and the SP8 threshold, which must be higher than the SP7 threshold, may be in the range of 24-40 millibar. Alternatively, the thresholds of SP3, SPS and SP7 may be identical and may be in the range of 7-20 millibar.

Disposed in pressure communication with inflation/deflation channel 452 as it extends from second inflation/deflation pump assembly 406 to the interior of an endoscope tool balloon, such as balloon 314 (FIG. 10), is a vacuum level indicator SV, which is preferably a binary vacuum indicator, providing an indication to computerized controller 402 whether the vacuum in inflation/deflation channel 452 thereat is above a predetermined pressure threshold.

It is appreciated that one or more of pressure level indicators SP1-SP8 and vacuum level indicator SV may be replaced by at least one differential continuous pressure/vacuum sensor, such as a Board Mount Pressure/Vacuum sensor, Part Number NSC-DIP-DR-150PD-UNV, commercially available from Honeywell International Inc.

Figure 14:
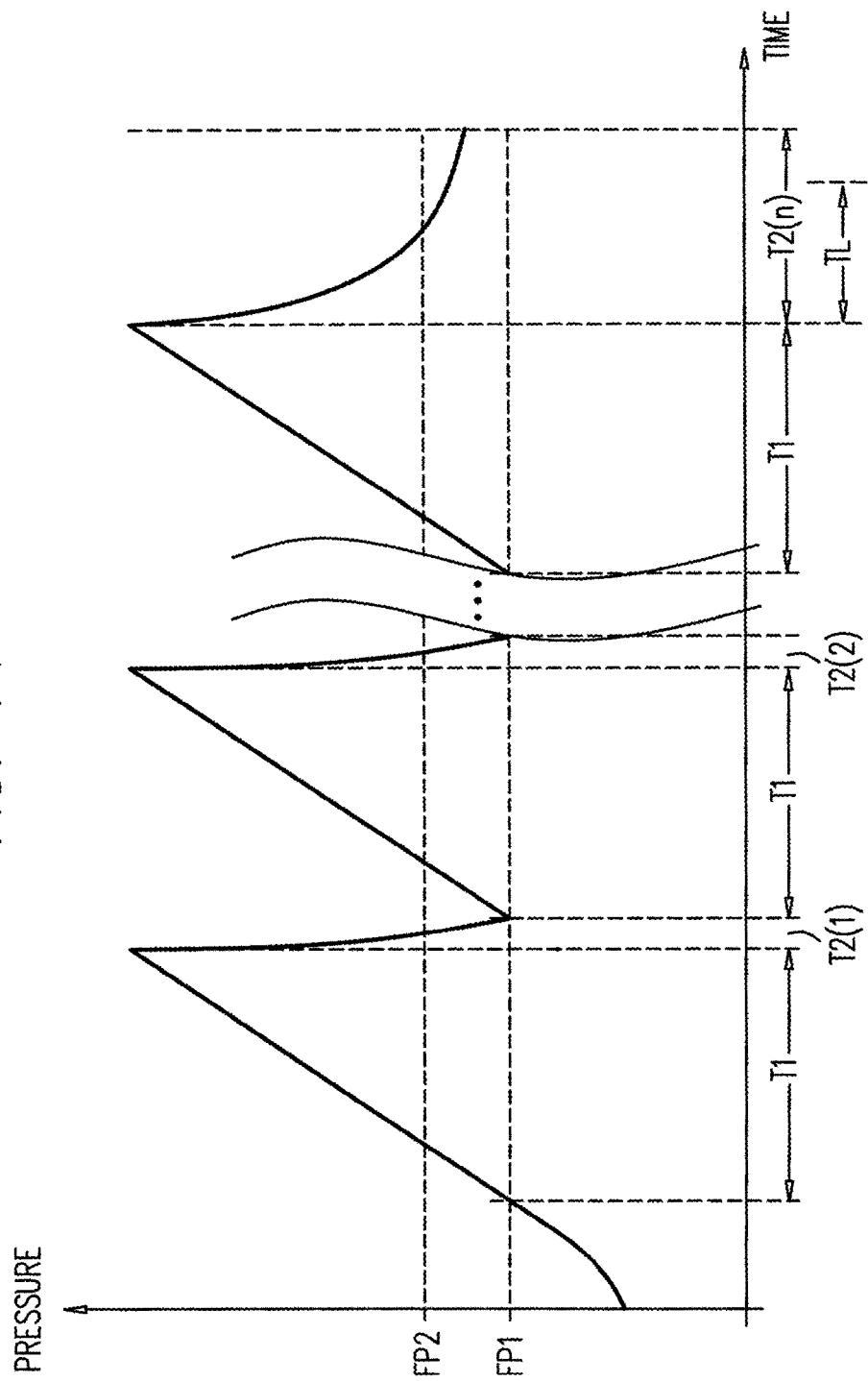
FIG. 14 is a simplified balloon pressurization diagram which illustrates a preferred open loop pressurization procedure operative in accordance with a preferred embodiment of the present invention.

Reference is now made to FIGS. 13A & 13B, which are together a simplified flow chart illustrating a preferred mode of operation of the balloon inflation/deflation system of FIG. 12 and to FIG. 14, which is a simplified balloon pressurization diagram which illustrates a preferred open loop pressurization procedure operative in accordance with a preferred embodiment of the present invention.

Following insertion of an endoscope into a body passageway of a patient, such as the colon or the small intestine of a patient, and following locating a first balloon to be inflated, such as an endo scope balloon or an endo scope tool balloon, at a desired location in the body passageway, the following procedure takes place:

The operator selects an appropriate desired inflation pressure state for inflation of the first balloon. Typical selectable inflation. pressure states include the following:

| Function | Pressure range |
| --- | --- |
| Anchoring | Between FP1 and FP2 |
| Stretching I | Between FP3 and FP4 |
| Stretching II | Between FPS and FP6 |
| Stretching III | Between FP7 and FP8 |

When seeking to anchor the first balloon to the tubular body portion, the operator, using the user interface 400 (FIG. 12), typically selects the anchoring pressure range corresponding to the Anchoring State.

When seeking to stretch the tubular body portion in accordance with a preferred embodiment of the present invention, the operator, using the user interface 400 (FIG. 12), typically selects one of the above intermediate pressure ranges corresponding to Stretching States I, II or III. depending on one or more of the following factors:
- the interior cross sectional diameter of the tubular body portion at the location of the first balloon;
- the extent of bending of the tubular body portion at the location of the first balloon;
- the specific tubular body portion at which the balloon is located, for example the right colon, the transverse colon, the left colon, the ileum, the jejunum, the esophagus and the duodenum; and
- the extent of stretching which appears to be required in order to achieve acceptable detection of polyps and other potential and actual pathologies.

It is a particular feature of a preferred embodiment of a balloon inflation subsystem of the present invention, such as balloon inflation/deflation system 130, that it is operative for either manual or automatic switching between the anchoring pressure and the suitable slidable frictional engagement pressure, as well as between different slidable frictional engagement pressure states, at any time during operation thereof, as needed in the course of the endoscopy procedure.

Next, the operator, using the user interface 400 (FIG. 12), initiates inflation of the first balloon, as by pressing on an F-Inflate button.

At this stage, the computerized controller governs the precise sequence of operations, which are described hereinbelow:

A balloon inflation safety check routine is carried out. This preferably includes verification of proper operation of the relevant ones of pressure indicators FP1-FPS; verification of proper operation of relevant ones of valves 416, 420 and 424 and verification of proper operation of pressure pump 408.

If anchoring has been selected, the first balloon is inflated to a pressure which is suitable for balloon anchoring. It is a particular feature of the present invention that inflation of the first balloon is carried out in an open loop inflation process. The open loop inflation process, such as that described in detail hereinbelow, enables safe and reliable and highly time efficient balloon inflation when the pressure indicators FP1-FPS are located in the inflation/deflation system 130 (FIGS. 1 & 10) rather than at the balloon being inflated.

In contrast to closed-loop prior art balloon inflation, an open-loop balloon inflation according to a preferred embodiment of an inflation/deflation system of the present invention is characterized by performing an automatic inflation sequence, which includes at least one step of balloon inflation over a predetermined time duration, notwithstanding the exceedance of a preset inflated balloon pressure by the pressure measured in an inflated balloon pressure indicator. The balloon inflation predetermined time duration is short enough to prevent over-inflation in the inflated balloon and consequentially potential damage to the body passageway under inspection. The automatic inflation sequence of the present invention provides inflation of the balloon over a substantially larger proportion of the overall inflation time than prior art closed loop inflation sequences, as will be described hereinbelow.

A preferred open loop inflation process is described hereinbelow with particular reference to FIG. 14:

The first balloon is inflated by opening valve 416 and operating pressure pump 408, with valves 420 and 424 being closed, until pressure indicator FP1 indicates exceedance of its threshold, typically 60 millibars, and continues thereafter for a further predetermined time T1.

Valve 416 is then closed and valve 424 is opened. In the meantime, due to the air flow to the balloon between pressure indicator FP1 and the balloon, the pressure as measured by pressure indicator FP1 decreases. The elapsed time T2(1) from closing of valve 416 to an indication by pressure indicator FP1 that the pressure threat is below its threshold is recorded.

If T2(1) is not longer than a predetermined time duration TL, the first balloon is again inflated by opening valve 416 and continuing to operate pressure pump 408, with valves 420 and 424 being closed, until pressure indicator FP1 again indicates exceedance of its threshold, typically 60 millibars, and continues thereafter for a further predetermined time T1.

Thereafter, valve 416 is again closed and valve 424 is again opened. In the meantime, due to the air flow to the balloon between pressure indicator FP1 and the balloon, the pressure as measured by pressure indicator FP1 decreases. The elapsed time T2(2) from this second closing of valve 416 to a second indication by pressure indicator FP1 that the pressure threat is below its threshold is also recorded.

If T2(2) is not longer than predetermined time duration TL, the foregoing procedure is repeated up to n times until T2(n) is longer than predetermined time duration TL. Once T2 is longer than TL, the first balloon is deemed to be inflated to within the designated pressure range.

It is appreciated that T1 is fixed and is such that it is always substantially greater than TZ(1), typically by 0.5-1.5 orders of magnitude. T1 is also selected such that the volume of air supplied to the balloon over duration T1 can never be such as to cause potentially dangerous over-inflation of the balloon.

T2 is determined in part by the physical characteristics of the air passage connecting the balloon with the inflation/deflation system and is also a function of the current extent of inflation of the balloon, the greater the extent of inflation of the balloon, the longer is T2.

Predetermined time duration TL may be fixed or may be a function of T2 and preferably more specifically a function of T2(1). In accordance with an embodiment of an inflation/deflation system of the present invention, TL is described by the formula:

$$TL = X*T2(1);$$

where X is a factor larger than one, and typically between 1.4 and 4.

Preferably, T1 is in the range of 0.3-1.5 seconds. More preferably, T1 is in the range of 0.5-1 second. More preferably, T1 is in the range of 0.6-0.8 seconds. In accordance with a specific preferred embodiment of the present invention, T1 is approximately 0.7 seconds. Correspondingly, when an endoscope balloon is inflated, T2(1) is typically in the range of 15-80 milliseconds and in most cases in the range of 30-50 milliseconds. When an endoscope tool balloon is inflated, T2(1) is typically in the range of 0.1-0.45 seconds and in most cases in the range of 0.2-0.35 seconds.

It is a particular feature of a balloon inflation/deflation system of the present invention that the inflation duty cycle, i.e. the ratio of time when the balloon is being inflated to the ratio of time when the balloon is not being inflated, is substantially greater than the inflation duty cycle in prior art balloon inflation/deflation systems.

As noted above, the inflation duty cycle of a preferred embodiment of the present invention is expressed as the ratio of T1 to T2, whereas in the prior art, closed loop system, the inflation duty cycle is expressed as the ratio of TCL to T2, where TCL is the time duration from the opening of the equivalent of valve 416 to termination of inflation when the measured pressure at the equivalent of pressure indicator FP1 exceeds its threshold and T2 is the same time duration employed in the present invention, i.e. the time duration from closing the equivalent of valve 416 to the time that the measured pressure at the equivalent of pressure indicator FP1 no longer exceeds its threshold.

In practice, the inflation duty cycle as defined above for the present invention may be between 2 and 35, while the inflation duty cycle for a corresponding prior art closed loop system would be 0.5-1.5. Preferably, the inflation duty cycle as defined above for the present invention is at least 2. More preferably, the inflation duty cycle as defined above for the present invention is at least 5. Yet more preferably, the inflation duty cycle as defined above for the present invention is at least 10.

It is appreciated that time efficiency of balloon inflation is a positive function of the inflation duty cycle and thus it is appreciated that the present invention has a time efficiency which is substantially greater than that of a corresponding prior art closed loop system. The balloon inflation time efficiency provided by a preferred embodiment of the present invention is improved at least by a factor of between 1.5 and 4, which normally means that a typical balloon inflation procedure for an endoscope tool balloon takes 3 seconds as compared with 8 seconds for a typical balloon inflation procedure for an endoscope tool balloon in a corresponding prior art closed loop inflation system.

At this stage, a balloon pressure maintenance procedure is carried out until a balloon deflation instruction is provided by the operator, such as by pressing an F-deflate button on the user interface 400. As described in greater detail in FIG. 13B, the balloon pressure maintenance procedure seeks at all times to have pressure indicator FP1 indicate that its threshold is exceeded and to have pressure indicator FP2 indicate that its threshold is not exceeded.

Should the threshold of pressure indicator FP2 be exceeded, valves 416 and 424 are both opened until pressure indicator FP2 indicates that its threshold is no longer exceeded. Should the threshold of pressure indicator FP1 not be exceeded, the pressure pump 408 is operated with valve 416 being open and valve 424 being closed until pressure indicator FP2 indicates exceedance of its threshold, at which point valve 416 is closed and valve 424 is opened.

Should the threshold of pressure indicator FP2 continue to be exceeded for a time duration TM following closing of valve 416, valves 416 and 424 are both opened until pressure, indicator FP2 indicates that its threshold is no longer exceeded. At this stage or earlier as appropriate, pressure pump 408 may be turned off.

The foregoing description relates to the anchoring function. If, instead of the anchoring function, one of the three stretching functions I, II or III is desired, the desired stretching function is selected by the operator via the user interface 400. A procedure which is substantially identical to that described above is carried out with the only difference being that the pressure range and the corresponding pair of pressure indicators are those associated with the selected stretching function.

Thus, if the operator selects stretching function I, the pressure indicators FP3 and FP4 replace respective pressure indicators FP1 and FP2 in the foregoing explanation. Similarly, if the operator selects stretching function II, the pressure indicators FP5 and FP6 replace respective pressure indicators FP1 and FP2 in the foregoing explanation and in the same manner, if the operator selects stretching function III, the pressure indicators FP7 and FP8 replace respective pressure indicators FP1 and FP2 in the foregoing explanation.

It is appreciated that the foregoing explanation applies equally to inflation of the second balloon and in such a case, the designations FP in the foregoing explanation are replaced by SP.

It is a particular feature of the present invention that the inflation/deflation system described hereinabove with reference to FIG. 12, by employing the open-loop inflation procedure and the balloon pressure maintenance procedure described hereinabove with reference to FIGS. 13A & 13B, is operative to automatically maintain inflation of the inflated balloon at a selected anchoring pressure or a selected slidable frictional engagement pressure as the balloon is displaced at various locations along the length of the body passageway, notwithstanding variations in the cross sectional area thereof.

Deflation of the first and second balloons may readily be achieved by the operator using the user interface 400. The operator may press on an F-deflate button or an S-deflate button respectively, causing the computerized controller 402 to carrying a deflation sequence as follows:

The deflation sequence for the first or second balloon preferably includes operating the corresponding vacuum pump 410 or 450 and during operation opening respective valves 420 or 460, while respective valves 416 or 456 are closed. This causes air to be drawn out of the respective balloon until a respective vacuum indicator FV or SV indicates exceedance of a predetermined vacuum threshold, at which time the corresponding valve 420 or 460 is closed and the corresponding vacuum pump 410 or 450 is deactivated.

It is appreciated that the inflation/deflation system described hereinabove with reference to FIGS. 12-13B is operative for providing inflation and/or deflation of generally any suitable type of a balloon-equipped endoscopic device, such as a balloon-equipped endoscope or a balloon-equipped endoscope tool.

It is also appreciated that in most procedures, only a single balloon will be inflated. The inflation/deflation system described hereinabove with reference to FIGS. 12-13B includes functionality for inflating two balloons, which may include one endoscope balloon and one endoscope tool balloon or alternatively two endoscope balloons or two tool balloons. This functionality is provided in the inflation/deflation system in order to enable universal use thereof whether or not an endoscope tool balloon is used and whether or not one or more endoscope balloons are used. Furthermore, the inflation/deflation system described hereinabove with reference to FIGS. 12-13B is useful in carrying out double balloon procedures such as those described in applicant/assignee's Published PCT Applications No. WO2005/074377, published on Aug. 18, 2005; WO2007/017854, published on Feb. 15, 2007; and WO 2011/111040, published on Sep. 15, 2011, the disclosures of which are hereby incorporated by reference.

It is additionally appreciated that the inflation/deflation system as described hereinabove with reference to FIGS. 12-13B preferably includes real-time automatic leak monitoring functionality such as that described in applicant/assignee's Published PCT Application No. WO 2011/111040, published on Sep. 15, 2011, the disclosure of which is hereby incorporated by reference.

It will be appreciated by persons skilled in the art that the present invention is not limited by what has been particularly shown and described herein above. Rather the scope of the present invention includes both combinations and subcombinations of the various features described hereinabove as well as variations and modifications which would occur to persons skilled in the art upon reading the specifications and which are not in the prior art.

What is claimed is:

1. A method for performing an endoscopy, comprising:
   advancing an endoscope through an intestine, the endoscope comprising a viewing portion positioned at a distal end and a balloon mounted at the distal end of the endoscope, the balloon mounted entirely and completely rearwardly of the viewing portion and configured for generally circumferential slidable frictional engagement with an interior wall of the intestine, wherein the balloon extends radially outward from the endoscope;
   automatically inflating the balloon to a predetermined anchoring pressure range via a controller upon a user selection of the predetermined anchoring pressure range;
   automatically deflating or inflating the balloon to a pressure value within a predetermined slidable frictional engagement pressure range via the controller upon a user selection of the predetermined slidable frictional engagement pressure range, the predetermined slidable frictional engagement pressure range being lower than a pressure value within an anchoring pressure range of the balloon; and
   retracting the endoscope through the intestine while maintaining the balloon pressure within the predetermined slidable frictional engagement pressure range such that during retraction of the endoscope through the intestine natural folds within the intestine are unfolded by engagement of the balloon with the interior wall of the intestine such that features of interest within the intestine become visible to the viewing portion.

2. The method of claim 1, wherein the balloon is configured such that the balloon is not visible to the viewing portion during retraction of the endoscope.

3. The method of claim 1, wherein during retraction of the endoscope, the balloon is configured to enable systematic visual inspection of the intestine.

4. The method of claim 1, wherein the slidable frictional engagement pressure is not higher than 35 millibar.

5. The method of claim 1, wherein the features of interest comprise polyps.

6. The method of claim 1, wherein circumferential engagement of the balloon with the interior wall of the intestine produces axial stretching of the interior wall of the intestine.

7. The method of claim 6, wherein axial stretching of the interior wall comprises axial stretching of the interior wall by at least 35%.

8. The method of claim 7, wherein axial stretching of the interior wall comprises axial stretching of the interior wall by at least 60%.

9. The method of claim 1, wherein the balloon comprises silicone.

10. The method of claim 1, wherein a ratio between a pressure value within the anchoring pressure range and a pressure value within the predetermined slidable frictional engagement pressure range is from 1.3-7.

11. A method for performing an endoscopy comprising:
    advancing an endoscope through an intestine, the endoscope comprising a viewing portion positioned at a distal end and a balloon mounted to the endoscope entirely and completely rearwardly of the viewing portion such that the balloon is not visible during retraction of the endoscope, the balloon configured for slidable frictional engagement with an interior wall of the intestine, wherein the balloon extends radially outward from the endoscope;

automatically inflating the balloon to a predetermined anchoring pressure range via a controller upon a user selection of the predetermined anchoring pressure range;

automatically deflating or inflating the balloon to a pressure value within a predetermined slidable frictional engagement pressure range via the controller upon a user selection of the predetermined slidable frictional engagement pressure range, the predetermined slidable frictional engagement pressure range being lower than a pressure value within an anchoring pressure range of the balloon; and retracting the endoscope through the intestine while maintaining the balloon pressure within the predetermined slidable frictional engagement pressure range such that during retraction of the endoscope through the intestine, natural folds within the intestine are unfolded by engagement of the balloon with the interior wall of the intestine such that features of interest within the intestine become visible to the viewing portion.

12. The method of claim 11, wherein the slidable frictional engagement pressure is not higher than 35 millibar.

13. The method of claim 11, wherein engagement of the balloon with the interior wall of the intestine produces axial stretching of the interior wall of the colon.

14. The method of claim 13, wherein axial stretching of the interior wall comprises axial stretching of the interior wall by at least 35%.

15. The method of claim 14, wherein axial stretching of the interior wall comprises axial stretching of the interior wall by at least 60%.

16. The method of claim 11, wherein the features of interest comprise polyps.

17. The method of claim 11, wherein the balloon comprises silicone.

18. The method of claim 11, wherein a ratio between a pressure value within the anchoring pressure range and a pressure value within the predetermined slidable frictional engagement pressure range is from 1.3-7.

* * * * *

UNITED STATES PATENT AND TRADEMARK OFFICE
CERTIFICATE OF CORRECTION

PATENT NO. : 11,247,029 B2
APPLICATION NO. : 16/665268
DATED : February 15, 2022
INVENTOR(S) : Terliuc et al.

It is certified that error appears in the above-identified patent and that said Letters Patent is hereby corrected as shown below:

In the Drawings

On Sheet 13 of 14, Fig. 13B, Line 3, delete "MAINTANANCE" and insert --MAINTENANCE--.

In the Specification

In Column 3, Line 40, delete "endo scope" and insert --endoscope--.

In Column 6, Line 46, delete "a ·" and insert --a--.

In Column 6, Line 59, delete "endo scope" and insert --endoscope--.

In Column 10, Line 4, delete "accordance:" and insert --accordance--.

In Column 10, Line 20, delete "functionality." and insert --functionality--.

In Column 13, Line 49, delete "endo scope" and insert --endoscope--.

In Column 16, Line 6, delete "endo scope" and insert --endoscope--.

In Column 17, Line 46, delete "Carl-Bosche" and insert --Carl-Bosch--.

In Column 23, Line 21, delete "SA, SB, SC & SD," and insert --5A, 5B, 5C & 5D,--.

In Column 23, Line 29 (Approx.), delete "SA-SD" and insert --5A-5D--.

In Column 23, Lines 46-47, delete "SC & SD" and insert --5C & 5D--.

In Column 24, Line 20, delete "SB" and insert --5B--.

Signed and Sealed this
Twenty-fourth Day of May, 2022

Katherine Kelly Vidal
*Director of the United States Patent and Trademark Office*

CERTIFICATE OF CORRECTION (continued)
U.S. Pat. No. 11,247,029 B2

In Column 24, Line 23, delete "SA-SD)" and insert --5A-5D)--.

In Column 26, Line 9, delete "endo scope," and insert --endoscope,--.

In Column 27, Lines 22-23, delete "endo scope" and insert --endoscope--.

In Column 27, Line 49, delete "colon" and insert --colon.--.

In Column 28, Line 6, delete "line." and insert --line--.

In Column 28, Line 22, delete "Fin" and insert --F in--.

In Column 29, Line 59, delete "FPS" and insert --FP5--.

In Column 29, Line 64, delete "FPS" and insert --FP5--.

In Column 31, Line 18, delete "SPS" and insert --SP5--.

In Column 31, Line 23 (Approx.), delete "SPS" and insert --SP5--.

In Column 31, Line 50, delete "endo scope" and insert --endoscope--.

In Column 31, Line 50, delete "endo scope" and insert --endoscope--.

In Column 31, Line 55 (Approx.), delete "inflation." and insert --inflation--.

In Column 31, Line 61, delete "FPS" and insert --FP5--.

In Column 32, Line 5, delete "III." and insert --III--.

In Column 32, Line 34, delete "FPS;" and insert --FP5;--.

In Column 32, Line 45, delete "FPS" and insert --FP5--.

In Column 33, Line 30, delete "TZ" and insert --T2--.